United States Patent [19]

Hlasta et al.

[11] Patent Number: 5,378,720
[45] Date of Patent: Jan. 3, 1995

[54] SACCHARIN DERIVATIVE PROTEOLYTIC ENZYME INHIBITORS

[75] Inventors: Dennis J. Hlasta, Lower Salford Township, Montgomery County, Pa.; James H. Ackerman, Albany; Albert J. Mura, Rochester, both of N.Y.; Ranjit C. Desai, Towamencin Township, Montgomery County, Pa.

[73] Assignee: Sterling Winthrop Inc., New York, N.Y.

[21] Appl. No.: 66,805

[22] Filed: May 25, 1993

Related U.S. Application Data

[63] Continuation-in-part of Ser. No. 810,265, Dec. 19, 1991, abandoned.

[51] Int. Cl.$^6$ .............. A61K 31/425; A61K 31/535; C07D 417/14; C07D 417/12
[52] U.S. Cl. .............. 514/373; 548/210; 544/135; 514/233.8
[58] Field of Search .............. 548/210; 514/373

[56] References Cited

U.S. PATENT DOCUMENTS

| | | | |
|---|---|---|---|
| 2,855,401 | 10/1958 | Barber et al. | 514/373 |
| 3,220,940 | 11/1965 | Brown et al. | 514/372 |
| 4,195,023 | 3/1980 | Mulvey et al. | 514/373 |
| 4,276,298 | 6/1981 | Jones et al. | 514/372 |
| 5,128,339 | 7/1992 | Dunlap et al. | 514/373 |

FOREIGN PATENT DOCUMENTS

| | | |
|---|---|---|
| 253092 | 1/1988 | European Pat. Off. . |
| 483928A1 | 5/1992 | European Pat. Off. . |
| 2321288 | 3/1977 | France . |
| WO9013549 | 11/1990 | WIPO . |

OTHER PUBLICATIONS

Sunket et al., J. Med. Chem. 31 1886–1890 (1988).

*Primary Examiner*—Joseph Paul Brust
*Assistant Examiner*—MarySusan H. Gabilan
*Attorney, Agent, or Firm*—Michael D. Alexander; Paul E. Dupont

[57] ABSTRACT

Compounds having the structural formula

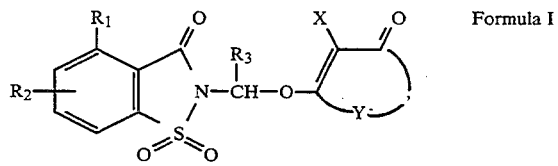

Formula I which inhibit the enzymatic activity of proteolytic enzymes, and processes for preparation thereof, method of use thereof in treatment of degenerative diseases and pharmaceutical compositions thereof are disclosed.

44 Claims, No Drawings

5,378,720

SACCHARIN DERIVATIVE PROTEOLYTIC ENZYME INHIBITORS

CROSS REFERENCE TO RELATED APPLICATIONS

This application is a continuation-in-part of our prior copending application Ser. No. 07/810,265, filed Dec. 19, 1991, now abandoned.

BACKGROUND OF THE INVENTION

1. Field of the Invention

The invention relates to saccharin derivatives which inhibit the enzymatic activity of proteolytic enzymes, to processes for preparation thereof, to method of use thereof in treatment of degenerative diseases and to pharmaceutical compositions thereof.

2. Information Disclosure Statement

Inhibitors of proteolytic enzymes are useful in treatment of degenerative disorders such as emphysema, rheumatoid arthritis and pancreatic in which proteolysis is a substantive element. Serine proteases are the most widely distributed class of proteolytic enzymes. Some serine proteases are characterized as chymotrypsin-like or elastase-like based upon their substrate specificity. Chymotrypsin and chymotrypsin-like enzymes normally cleave a peptide bond in a protein at a site at which the amino acid on the carbonyl side is Trp, Tyr, Phe, Met, Leu or other amino acid which contains an aromatic or a large alkyl side chain. Elastase and elastase-like enzymes normally cleave a peptide bond at a site at which the amino acid residue on the carbonyl side of the bond is Ala, Val, Ser, Leu or other small amino acid. Both chymotrypsin-like and elastase-like enzymes are found in leukocytes, mast cells and pancreatic juice in higher organisms, and are secreted by many types of bacteria, yeast and parasites.

Dunlap et al. PCT Application WO 90/13549 published Nov. 15, 1990 describes a series of 2-substituted saccharin derivatives useful as proteolytic enzyme inhibitors.

Barber et al., U.S. Pat. No. 2,855,401, issued Oct. 7, 1958, disclose compounds of the formula:

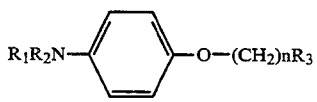

wherein $R_1$ and $R_2$ are each selected from hydrogen, lower-alkyl and lower hydroxyalkyl, n is an integer from 5 to 9 and $R_3$ is a group selected from methanesulphonamido, benzenesulphonamido and o-sulphonbenzimido. The compounds are said to be useful in the treatment of bilharziasis.

Brown et al., U.S. Pat. No. 3,220,940, issued Nov. 30, 1965, disclose the use in acidic nickel baths of the compounds of the formula:

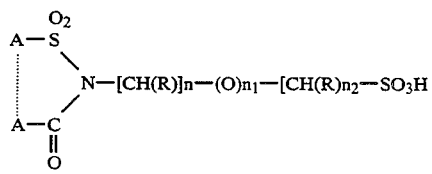

or the Ni, Na, Co, K, Li, Mg, etc. sulfonate salts thereof, wherein A is selected from the group consisting of the benzene, biphenyl and naphthalene rings, R is selected from the group consisting of H, OH, Cl, Br, $SO_3H$ and $CH_3$, n is an integer from 1 to 4 inclusive, $n_1$ is 0 or 1, $n_2$ is zero, 1 or 2, and when $n_2$ is zero then $n_1$ is zero.

Sunket et al., European Patent Application 253092, published Jan. 20, 1988, disclose 2-saccharinyl-lower-alkyl-1,4-dihydropyridine-3-carboxylates having a platelet aggregation inhibitory and antithrombotic activities. A substantially similar disclosure can be found in Sunket et al., J. Med. Chem. 31, 1886–1890 (1988).

Mulvey et al., U.S. Pat. No. 4,195,023, issued Mar. 25, 1980, disclose $R_1$-2-$R_2$ CO-1,2-benzisothiazol-3-ones, where $R_1$ is halogen, alkoxy, alkylamino, dialkylamino, alkoxycarbonyl, amino, nitro or hydrogen in the benzenoid ring and $R_2$ is hydrogen, alkyl, alkenyl, alkynyl, cycloalkyl, halophenyl, heteroaryl or substituted heteroaryl $R_1$-2-A-CO saccharins, where $R_1$ has the same meanings as the benzenoid ring substituents in the 1,2-benzisothiazol-3-ones and A is alkyl, alkenyl, alkynyl, cycloalkyl, fluorophenyl, heteroaryl or substituted heteroaryl. The compounds are said to have elastase inhibitory activity and to be useful in the treatment of emphysema. A similar disclosure is found in French Patent 2,321,288, published Mar. 18, 1977.

Dunlap et al., European Patent Application 483928A1, published May 6, 1992, disclose 4-$R^4$-$R^5$ 2-saccharinylmethyl aryl carboxylates and 4,5,6,7-tetrahydro-2-saccharinylmethyl aryl carboxylates which are said to have protease enzyme inhibitory activity and be useful in the treatment of degenerative diseases. A similar disclosure is found in Dunlap et al., U.S. Pat. No. 5,128,339, issued Jul. 7, 1992.

Jones et al., U.S. Pat. No. 4,276,298, issued Jun. 30, 1981, disclose 2-R-1,2-benzisothiazolinone-1,1-dioxides, where R is phenyl substituted by fluoro, dinitro, trifluoromethyl, cyano, alkoxycarbonyl, alkylcarbonyl, carboxyl, carbamoyl, alkylacylamino, alkylsulfonyl, N,N-dialkylsulfamoyl, trifluoromethoxy, trifluoromethylthio, trifluoromethylsulfonyl and trifluoromethylsulfonyl or pyridyl substituted the same as R when R is phenyl except that pyridyl may also be mononitro substituted. The compounds are said to have protease enzyme inhibitory activity, especially elastase inhibitory activity, and to be useful in the treatment of emphysema, rheumatoid arthritis "and other inflammatory diseases."

SUMMARY OF THE INVENTION

In a first composition of matter aspect the invention is a compound having the structural formula

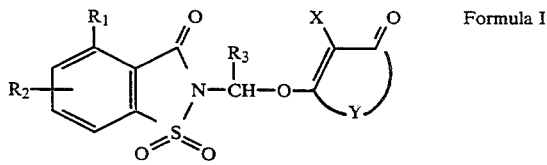

Formula I $R_1$ is hydrogen, halo, lower-alkyl, perfluoro-lower-alkyl, perchloro-lower-alkyl, lower-alkenyl, lower-alkynyl, cyano, amino, lower-alkylamino, di-lower-alkylamino, lower-alkoxy, benzyloxy, lower-alkoxycarbonyl or phenyl; and $R_2$ is from one to three substituents at any or all of the 5-, 6- and 7-positions and is selected from the group consisting of hydrogen, lower-alkyl, cycloalkyl, amino-lower-alkyl, lower-alkylamino-lower-alkyl, di-lower-alkylamino-lower-alkyl, hydroxy-lower-alkyl, lower-alkoxy-lower-alkyl, perfluoro-lower-alkyl, perchloro-lower-alkyl, formyl, cyano, carboxy, aminocarbonyl, R-oxycarbonyl, B=N, 1-lower-alkyl-2-pyrrolyl, lower-alkylsulfonylamino, perfluoro-lower-alkylsulfonylamino, perchloro-lower-alkylsulfonylamino, nitro, hydroxy, R-carbonyloxy, lower-alkoxy, cycloalkoxy, B=N-lower-alkoxy, hydroxy-lower-alkoxy, poly-hydroxy-lower-alkoxy or acetal or ketal thereof, lower-alkoxy-lower-alkoxy, poly-lower-alkoxy-lower-alkoxy, hydroxy-poly-lower-alkylenoxy, lower-alkoxy-poly-lower-alkylenoxy, B=N-carbonyloxy, carboxy-lower-alkoxy, R-oxycarbonyl-lower-alkoxy, methylenedioxy, di-lower alkyl-phosphonyloxy R-thio, R-sulfinyl, R-sulfonyl, perfluoro-lower alkylsulfonyl, perchloro-lower-alkylsulfonyl, aminosulfonyl, lower-alkylaminosulfonyl, di-lower-alkylaminosulfonyl, halo, B=N—(CH$_2$)pC(O)(CH$_2$)p'—O—,—O—(CH$_2$-)p—(5—((CH$_2$)p'—B=N—2-furanyl), and R-oxy-lower-alkoxy wherein p and p' are integers from 1 to 4, R is lower-alkyl, phenyl or phenyl-lower-alkyl, phenyl can have from one to three substituents selected from the group consisting of lower-alkyl, B=N-carbonyl, B=N, lower-alkoxy, B=N-lower-alkoxy and halo and B=N is amino, lower-alkylamino, di-lower-alkylamino, carboxy-lower-alkylamino, 1-pyrrolidinyl, 1-piperidinyl, 1-azetidinyl, 4-morpholinyl, 1-piperazinyl, 4-lower-alkyl-1-piperazinyl, 4-benzyl-1-piperazinyl or 1-imidazolyl;

R$_3$ is hydrogen, lower-alkyl or phenyl;

X is hydrogen, nitro, halo, lower-alkyl, perfluoro-lower-alkyl, perchloro-lower-alkyl, phenyl, phenyl-lower-alkyl, phenylcarbonyl, pyridyl-lower-alkyl, formyl, lower-alkanoyl, carboxy, lower-alkoxycarbonyl, aminocarbonyl, lower-alkylaminocarbonyl, di-lower-alkylaminocarbonyl, cyano, B=N, B=N-lower-alkyl, B=N-lower-alkanoyl, B=N-lower-alkoxycarbonyl, hydroxy, lower-alkoxy, phenyloxy, B=N-lower-alkoxy, lower-alkylthio, phenylthio, lower-alkylsulfonyl, phenylsulfonyl or B=N-sulfonyl wherein phenyl is unsubstituted or has from one to three substituents selected from the group consisting of lower-alkyl, lower-alkoxy and halo and B=N is amino, lower-alkylamino, di-lower-alkylamino, carboxy-lower-alkylamino, 1-pyrrolidinyl, 1-piperidinyl, 1-azetidinyl, 4-morpholinyl, 1-piperazinyl, 4-lower-alkyl-1-piperazinyl, 4-benzyl-1-piperazinyl or 1-imidazolyl; and —Y— is the remaining atoms of a monocyclic or bicyclic, substituted or unsubstituted carbocyclic or heterocyclic ring system;

or a pharmaceutically acceptable acid addition salt thereof if the compound has a basic functional group or a pharmaceutically acceptable base addition salt thereof if the compound has an acidic functional group.

The compounds of Formula I inhibit the enzymatic activity of proteolytic enzymes and are useful in treatment of degenerative diseases.

Compounds within the ambit of Formula I above are those wherein

R$_1$ is hydrogen, halo, lower-alkyl, perfluoro-lower-alkyl, perchloro-lower-alkyl, lower-alkenyl, lower-alkynyl, cyano, amino, lower-alkylamino, di-lower-alkylamino, lower-alkoxy, benzyloxy, lower-alkoxycarbonyl or phenyl; and R$_2$ is from one to three substituents at any or all of the 5-, 6- and 7-positions and is selected from the group consisting of hydrogen, lower-alkyl, cycloalkyl, amino-lower-alkyl, lower-alkylamino-lower-alkyl, di-lower-alkylamino-lower-alkyl, hydroxy-lower-alkyl, lower-alkoxy-lower-alkyl, perfluoro-lower-alkyl, perchloro-lower-alkyl, formyl, cyano, carboxy, aminocarbonyl, R-oxycarbonyl, B=N, 1-lower-alkyl-2-pyrrolyl, lower-alkylsulfonylamino, perfluoro-lower-alkylsulfonylamino, perchloro-lower-alkylsulfonylamino, nitro, hydroxy, R-carbonyloxy, lower-alkoxy, cycloalkoxy, B=N-lower-alkoxy, hydroxy-lower-alkoxy, poly-hydroxy-lower-alkoxy or acetal or ketal thereof, lower-alkoxy-lower-alkoxy, poly-lower-alkoxy-lower-alkoxy, hydroxy-poly-lower-alkylenoxy, lower-alkoxy-poly-lower-alkylenoxy, B=N-carbonyloxy, carboxy-lower-alkoxy-R-oxycarbonyl-lower-alkoxy, methylenedioxy, di-lower-alkylphosphonyloxy R-thio, R-sulfinyl, R-sulfonyl, perfluoro-lower-alkylsulfonyl, perchloro-lower-alkylsulfonyl, aminosulfonyl, lower-alkylaminosulfonyl, di-lower-alkylaminosulfonyl and halo wherein R is lower-alkyl, phenyl or phenyl-lower-alkyl, phenyl can have from one to three substituents selected from the group consisting of lower-alkyl, B=N-carbonyl, B=N, lower-alkoxy, B=N-lower-alkoxy and halo and B=N is amino, lower-alkylamino, di-lower-alkylamino, carboxy-lower-alkylamino, 1pyrrolidinyl, 1-piperidinyl, 1azetidinyl, 4-morpholinyl, 1-piperazinyl, 4-lower-alkyl-1-piperazinyl, 4-benzyl-1-piperazinyl or 1-imidazolyl;

R$_3$ is hydrogen, lower-alkyl or phenyl;

X is hydrogen, nitro, halo, lower-alkyl, perfluoro-lower-alkyl, perchloro-lower-alkyl, phenyl, phenyl-lower-alkyl, phenylcarbonyl, pyridyl-lower-alkyl, formyl, lower-alkanoyl, carboxy, lower-alkoxycarbonyl, aminocarbonyl, lower-alkylaminocarbonyl, di-lower-alkylaminocarbonyl, cyano, B=N, B=N-lower-alkyl, B=N-lower-alkanoyl, B=N-lower-alkoxycarbonyl, hydroxy, lower-alkoxy, phenyloxy, B=N-lower-alkoxy, lower-alkylthio, phenylthio, lower-alkylsulfonyl, phenylsulfonyl or B=N-sulfonyl wherein phenyl is unsubstituted or has from one to three substituents selected from the group consisting of lower-alkyl, lower-alkoxy and halo and B=N is amino, lower-alkylamino, di-lower-alkylamino, carboxy-lower-alkylamino, 1-pyrrolidinyl, 1-piperidinyl, 1-azetidinyl, 4-morpholinyl, 1-piperazinyl, 4-lower-alkyl-1-piperazinyl, 4-benzyl-1-piperazinyl or 1-imidazolyl; and —Y— is the remaining atoms of a monocyclic or bicyclic, substituted or unsubstituted carbocyclic or heterocyclic ring system;

or a pharmaceutically acceptable acid addition salt thereof if the compound has a basic functional group or a pharmaceutically acceptable base addition salt thereof if the compound has an acidic functional group.

In a preferred composition of matter aspect the invention is a compound of Formula I wherein —Y— is —(CH$_2$)$_m$—, —C(=O)—, —(CH$_2$)$_m$—O—, —CHR—O—, —CR$_2$—O—, —C[(CH$_2$)$_n$]—O—, —C[CH$_2$CH$_2$N(R)CH$_2$CH$_2$]—O—, —(CH$_2$)$_m$—N(R-')—, —CHR—N(R')—, —CR$_2$—N(R')—, —C(R')=C(R')—O—, —C(R')=C(R')—N(R')—, —C(=O)—C(R")=C(R")—, —C(Z')=C(Z')—, —C(Z')=C(Z')—O—, —C(Z')=C(Z')—N(R')—, —N(Z")—C(Z")=N— or —N=C(Z")—N(Z")— wherein m is 1, 2, 3, or 4, n is 3, 4, or 5, R is the same or different lower-alkyl, phenyl or phenyl-lower-alkyl, R' is H or R, R" is H or R or the R" groups taken together with the carbon atoms to which they are bonded are furano, the Z' groups taken together with the carbon atoms to which they are bonded are benzo, furano, pyrido, pyrimidino or pyridazino, and the Z" groups taken together with the carbon or nitrogen atoms to which they are bonded are pyrido, pyrimidino or pyridazino wherein phenyl, benzo, furano, pyrido, pyrimidino or pyridazino can have from one to three substituents selected from the group consisting of lower-alkyl, B=N-carbonyl, B=N, lower-alkoxy, B=N-lower-alkoxy and halo wherein B=N is amino, lower-alkylamino, di-lower-alkylamino, (carboxy-lower-alkyl)amino, 1-pyrrolidinyl, 1-piperidinyl, 1-azetidinyl, 4-morpholinyl, 1-piperazinyl, 4-lower-alkyl-1-piperazinyl, 4-benzyl-1-piperazinyl or 1-imidazolyl.

Other compounds of Formula I above are those wherein:

$R_1$ is hydrogen, halo, lower-alkyl, perfluoro-lower-alkyl, perchloro-lower-alkyl, lower-alkenyl, lower-alkynyl, cyano, amino, lower-alkylamino, di-lower-alkylamino, lower-alkoxy, benzyloxy, lower-alkoxycarbonyl or phenyl; and $R_2$ is from one to three substituents at any or all of the 5-, 6- and 7-positions and is selected from the group consisting of hydrogen, lower-alkyl, cycloalkyl, amino-lower-alkyl, lower-alkylamino-lower-alkyl, di-lower-alkylamino-lower-alkyl, hydroxy-lower-alkyl, lower-alkoxy-lower-alkyl, perfluoro-lower-alkyl, perchloro-lower-alkyl, formyl, cyano, carboxy, aminocarbonyl, R-oxycarbonyl, B=N, 1-lower-alkyl-2-pyrrolyl, lower-alkylsulfonylamino, perfluoro-lower-alkylsulfonylamino, perchloro-lower-alkylsulfonylamino, nitro, hydroxy, R-carbonyloxy, lower-alkoxy, cycloalkoxy, B=N-lower-alkoxy, hydroxy-lower-alkoxy, poly-hydroxy-lower-alkoxy or acetal or ketal thereof, lower-alkoxy-lower-alkoxy, poly-lower-alkoxy-lower-alkoxy, hydroxy-poly-lower-alkylenoxy, lower-alkoxy-poly-lower-alkylenoxy, B=N-carbonyloxy, carboxy-lower-alkoxy, R-oxycarbonyl-lower-alkoxy, methylenedioxy, di-lower alkylphosphonyloxy R-thio, R-sulfinyl, R-sulfonyl, perfluoro-lower-alkylsulfonyl, perchloro-lower-alkylsulfonyl, aminosulfonyl, lower-alkylaminosulfonyl, di-lower-alkylaminosulfonyl, and halo, wherein R is lower-alkyl, phenyl or phenyl-lower-alkyl, phenyl can have from one to three substituents selected from the group consisting of lower-alkyl, R=N-carbonyl, B=N, lower-alkoxy, B=N-lower-alkoxy and halo and B=N is amino, lower-alkylamino, di-lower-alkylamino, carboxy-lower-alkylamino, 1-pyrrolidinyl, 1-piperidinyl, 1-azetidinyl, 4-morpholinyl, 1-piperazinyl, 4-lower-alkyl-1-piperazinyl, 4-benzyl-1-piperazinyl or 1-imidazolyl;

$R_3$ is hydrogen, lower-alkyl or phenyl;

X is hydrogen, nitro, halo, lower-alkyl, perfluoro-lower-alkyl, perchloro-lower-alkyl, phenyl, phenyl-lower-alkyl, phenylcarbonyl, pyridyl-lower-alkyl, formyl, lower-alkanoyl, carboxy, lower-alkoxycarbonyl, aminocarbonyl, lower-alkylaminocarbonyl, di-lower-alkylaminocarbonyl, cyano, B=N, B=N-lower-alkyl, B=N-lower-alkanoyl, B=N-lower-alkoxycarbonyl, hydroxy, lower-alkoxy, phenyloxy, B=N-lower-alkoxy, lower-alkylthio, phenylthio, lower-alkylsulfonyl, phenylsulfonyl or B=N-sulfonyl wherein phenyl is unsubstituted or has from one to three substituents selected from the group consisting of lower-alkyl, lower-alkoxy and halo and B=N is amino, lower-alkylamino, di-lower-alkylamino, carboxy-lower-alkylamino, 1pyrrolidinyl, 1-piperidinyl, 1-azetidinyl, 4-morpholinyl, 1-piperazinyl, 4-lower-alkyl-1-piperazinyl, 4-benzyl-1-piperazinyl or 1-imidazolyl; and Y— is C(Z''')=C(Z''')—S,— N=C(R''')—(N(R''')), or —C(R'''')=C(L)—N(L)— and wherein the Z''' groups taken together with the carbon atom to which they are bonded are benzo; the R''' groups taken together with the carbon or nitrogen atom to which they are bonded are (—CH$_2$)$_n$', —(CH$_2$)$_q$-N(R*)(CH$_2$)$_q'$— or thiazolo; the L groups are taken with the carbon or nitrogen atoms to which they are bonded are pyrido; n' is an integer from 3 to 5; R* is hydrogen, phenyl, phenyl-lower-alkyl, or lower-alkyl; q is 1 or 2; q' is 1 or 2, R'''' is hydrogen, cyano, CO$_2$L', SO$_2$L" or nitro; L' is hydrogen, lower-alkyl or di-lower-alkylamino, and L" is hydroxy; lower-alkoxy, di-lower-alkylamino or trifluoromethyl.

Still other compounds of the Formula I above are those wherein:

$R_1$ is hydrogen, halo, lower-alkyl, perfluoro-lower-alkyl, perchloro-lower-alkyl, lower-alkenyl, lower-alkynyl, cyano, amino, lower-alkylamino, di-lower-alkylamino, lower-alkoxy, benzyloxy, lower-alkoxycarbonyl or phenyl; and $R_2$ is from one to three substituents at any or all of the 5-, 6- and 7-positions and is selected from the group consisting of B=N—(CH$_2$)$_p$C(O)O(CH$_2$)$_{p'}$—O— and R-oxylower-alkoxy wherein p and p' are integers from 1 to 4, R is lower-alkyl, phenyl or phenyl-lower-alkyl, phenyl can have from one to three substituents selected from the group consisting of lower-alkyl, B=N-carbonyl, B=N, lower-alkoxy, B=N-lower-alkoxy and halo and B=N is amino, lower-alkylamino, di-lower-alkylamino, carboxy-lower-alkylamino, 1-pyrrolidinyl, 1-piperidinyl, 1-azetidinyl, 4-morpholinyl, 1piperazinyl, 4-lower-alkyl-1-piperazinyl, 4-benzyl-1-piperazinyl or 1-imidazolyl;

$R_3$ is hydrogen, lower-alkyl or phenyl;

X is hydrogen, nitro, halo, lower-alkyl, perfluoro-lower-alkyl, perchloro-lower-alkyl, phenyl, phenyl-lower-alkyl, phenylcarbonyl, pyridyl-lower-alkyl, formyl, lower-alkanoyl, carboxy, lower-alkoxycarbonyl, aminocarbonyl, lower-alkylaminocarbonyl, di-lower-alkylaminocarbonyl, cyano, B=N, B=N-lower-alkyl, B=N-lower-alkanoyl, B=N-lower-alkoxycarbonyl, hydroxy, lower-alkoxy, phenyloxy, B=N-lower-alkoxy, lower-alkylthio, phenylthio, lower-alkylsulfonyl, phenylsulfonyl or B=N-sulfonyl wherein phenyl is unsubstituted or has from one to three substituents selected from the group consisting of lower-alkyl, lower-alkoxy and halo and B=N is amino, lower-alkylamino, di-lower-alkylamino, carboxy-lower-alkylamino, 1-pyrrolidinyl, 1-piperidinyl, 1-azetidinyl, 4-morpholinyl, 1-piperazinyl, 4-lower-alkyl-1-piperazinyl, 4-benzyl-1-piperazinyl or 1-imidazolyl; and —Y— is the remaining atoms or a monocyclic or bicyclic, substituted or unsubstituted carbocyclic or heterocyclic ring system;

or a pharmaceutically acceptable acid addition salt thereof if the compound has a basic functional group or a pharmaceutically acceptable base addition salt thereof if the compound has an acidic functional group.

In a first process aspect the invention is the process for preparing a compound of Formula I which comprises condensing the corresponding compound having the structural formula

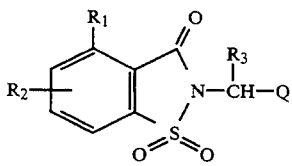

Formula II wherein Q is chloro or bromo with the corresponding compound having the structural formula

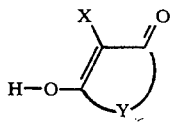

Formula III in the presence of a base or with a corresponding basic salt of the compound of Formula III.

In a second process aspect the invention is the method of treating a patient having a degenerative disease which comprises administering to the patient a proteolytic enzyme inhibiting amount of a compound of Formula I.

In a second composition of matter aspect the invention is a pharmaceutical composition for treatment of degenerative disease which comprises a proteolytic enzyme inhibiting concentration of a compound of Formula I in a pharmaceutical carrier.

DETAILED DESCRIPTION OF THE INVENTION INCLUSIVE OF THE PREFERRED EMBODIMENTS

The Compounds and Their Preparation

The part of the compound of Formula I having the structural formula

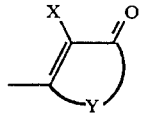

is also described below as having the formula —Z. The compound of Formula III is accordingly also described below as having the formula H—O—Z.

Saccharin is 1,2-benzisothiazol-(1H)-3-one-1,1-dioxide, and the compounds of Formula I, which are 2-[Z—O—CH($R_3$)]-4-$R_1$-(5,6 and/or 7)-$R_2$-1,2-benzisothiazol-(1H)-3-one-1,1-dioxides, are accordingly 2-[Z—O—CH($R_3$)]-4-$R_1$-(5,6 and/or 7)-$R_2$-saccharins.

In the compounds of Formulas I-III "corresponding" means that a defined variable in one formula has the same definition in another formula.

In lower-alkyl, perfluoro-lower-alkyl, perchloro-lower-alkyl, lower-alkoxycarbonyl, lower-alkylamino, di-lower-alkylamino, lower-alkoxy, the lower-alkylamino part of lower-alkylamino-lower-alkyl, the lower-alkylamino part of di-lower-alkylamino-lower-alkyl, the lower-alkoxy part of lower-alkoxy-lower-alkyl, carboxy-lower-alkylamino, 4-lower-alkyl-1-piperazinyl, 1-lower-alkyl-2-pyrrolyl, lower-alkylsulfonylamino, perfluoro-lower-alkylsulfonylamino, perchloro-lower-alkylsulfonylamino, the first lower-alkoxy part of lower-alkoxy-lower-alkoxy, the first lower-alkoxy part of poly-lower-alkoxy-lower-alkoxy, the lower-alkoxy part of lower-alkoxy-poly-lower-alkylenoxy, R-oxycarbonyl-lower-alkoxy, perfluoro-lower-alkylsulfonyl, perchloro-lower-alkylsulfonyl, lower-alkylaminosulfonyl, di-lower-alkylaminosulfonyl, 4-lower-alkyl-1-piperazinyl, phenyl-lower-alkyl, pyridyl-lower-alkyl, lower-alkylaminocarbonyl, di-lower-alkylaminocarbonyl, lower-alkylthio and carboxy-lower-alkylamino the carbon chain part thereof has from one to ten carbon atoms, preferably from one to four carbon atoms, and is branched or unbranched. In lower-alkenyl, lower-alkynyl, amino-lower-alkyl, the lower-alkyl part of lower-alkylamino-lower-alkyl, the lower-alkyl part of di-lower-alkylamino-lower-alkyl, hydroxy-lower-alkyl, the lower-alkyl part of lower-alkoxy-lower-alkyl, the lower-alkoxy part of B=N-lower-alkoxy, hydroxy-lower-alkoxy, polyhydroxy-lower-alkoxy, the second lower-alkoxy part of lower-alkoxy-lower-alkoxy, the second lower-alkoxy part of poly-lower-alkoxy-lower-alkoxy, the alkylenoxy part of hydroxy-poly-lower-alkylenoxy, the alkylenoxy part of lower-alkoxy-poly-lower-alkylenoxy, lower-alkanoyl, B=N-lower-alkyl, B=N-lower-alkanoyl and B=N-lower-alkoxycarbonyl the carbon chain part thereof has from two to ten carbon atoms, preferably from two to four carbon atoms, and is branched or unbranched. Alkylene is preferably 1,2-alkylene. Cycloalkyl and cycloalkoxy have from three to six ring carbon atoms and can be substituted by one or more lower-alkyl. Halo is fluoro, chloro, bromo or iodo.

$R_1$ is preferably primary or secondary alkyl of two to four carbon atoms or lower-alkoxy.

$R_2$ is preferably hydrogen, hydroxy, lower-alkoxy, cycloalkoxy, B=N-lower-alkoxy, hydroxy-lower-alkoxy, polyhydroxy-lower-alkoxy or acetal or ketal thereof, lower-alkoxy-lower-alkoxy, poly-lower-alkoxy-lower-alkoxy, hydroxy-poly-lower-alkylenoxy, lower-alkoxy-poly-lower-alkylenoxy, B=N-carbonyloxy, carboxy-lower-alkoxy, R-oxycarbonyl-lower-alkoxy, methylenedioxy or di-lower-alkylphosphonyloxy and, except methylenedioxy, is preferably located at the 6-position. Methylenedioxy can be located at the 5 and 6- or 6 and 7-positions.

In carrying out preparation of a compound of Formula I from a corresponding compound of Formula II and the corresponding compound of Formula III in the presence of a base, the base can be any base which is not itself a reactant under the reaction conditions and is preferably an alkali metal hydride, an alkali metal carbonate, an alkali metal alkoxide, a tri-lower-alkylamine, a thallous lower-alkoxide, 1,8-diazabicyclo[5,4,0]undec-7-ene or 7-methyl-1,5,7-triazobicyclo[4,4,0]dec-5-ene. Under the reaction conditions the base may form the basic salt of the compound of Formula III, which then reacts with the compound of Formula II. The basic salt of the compound of Formula III can also be formed separately and then condensed with the compound of Formula II and is preferably an alkali metal, especially cesium, or thallous salt thereof. The condensation is carried out in an organic solvent or mixture of organic solvents inert under the reaction conditions, for example acetone, methyl ethyl ketone, acetonitrile, tetrahydrofuran, diethyl ether, dimethylformamide, N-methylpyrrolidine, dichloromethane, xylene, toluene or a lower-alkanol or mixture thereof, at a temperature in the range from ambient temperature to the boiling temperature of the solvent or solvent mixture.

The compounds of Formulas II and III are known or are made by known methods or by methods described below.

A compound of Formula II wherein $R_3$ is hydrogen can be prepared by diazotizing the corresponding lower-alkyl 2-amino-3, 4 or 5-$R_2$-6-$R_1$-benzoate ester, chlorosulfonylating the resulting lower-alkyl 3, 4 or 5-$R_2$-6-$R_1$benzoate ester 2-diazonium salt with sulfur dioxide and cuprous chloride, and cyclizing the resulting lower-alkyl 2-chlorosulfonyl-3,4 or 5-$R_2$-6-$R_1$-benzoate ester with ammonia to form the corresponding compound having the structural formula:

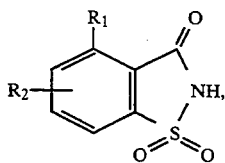

Formula IV hydroxymethylation of which with formaldehyde affords the corresponding 2-hydroxymethyl-4-$R_1$-(5, 6 or 7)-$R_2$-saccharin, displacement of whose hydroxy with chloride or bromide using, for example thionyl chloride, thionyl bromide, phosphorus trichloride or phosphorous tribromide affords the corresponding compound of Formula II.

A compound of Formula II wherein $R_3$ is hydrogen and Q is chloro can also be prepared in one step from the corresponding compound of Formula IV by chloromethylation with formaldehyde and chlorotrimethylsilane in the presence of a Lewis acid, for example stannic chloride.

A compound of Formula II wherein $R_3$ is lower-alkyl can be prepared by vinylating the corresponding compound of Formula IV with the corresponding substituted or unsubstituted vinyl ester of a lower-alkanoic acid in the presence of disodium palladium tetrachloride, then treating the resulting 2-(substituted or unsubstituted vinyl)-4-$R_1$-(5, 6 or 7)-$R_2$-saccharin with hydrogen chloride. Use of unsubstituted vinyl acetate, for example, affords the corresponding compound of Formula II wherein $R_3$ is methyl.

A compound of Formula II wherein $R_3$ is hydrogen or phenyl can be prepared by phenylthio-$R_3$-methylating the corresponding compound of Formula IV or basic salt thereof with the corresponding phenyl $R_3$-chloromethyl sulfide to form the corresponding 2-(phenylthio-$R_3$-methyl)-4-$R_1$-(5, 6 or 7)-$R_2$-saccharin and displacing phenylthio therefrom with chloro or bromo using, for example, sulfuryl chloride or sulfuryl bromide.

A compound of Formula IV can be prepared by lithiating the corresponding 2-$R_1$-3, 4 or 5-$R_2$-N,N-di-lower-alkylbenzamide with a lower-alkyl lithium, aminosulfonylating the resulting 2-$R_1$-3, 4 or 5-$R_2$-6-lithio-N,N-di-lower-alkylbenzamide with sulfur dioxide followed by hydroxylamine O-sulfonic acid or sulfuryl chloride followed by ammonia, and cyclizing the resulting 2-$R_1$-3, 4 or 5-$R_2$-6-aminosulfonyl-N,N-di-lower-alkylbenzamide in refluxing acetic acid.

A compound of Formula IV wherein $R_1$ is primary of secondary alkyl of two to four carbon atoms can be prepared by lithiating the corresponding compound of Formula IV wherein $R_1$ is methyl with two molar equivalents of a lower-alkyl lithium in an inert solvent, for example tetrahydrofuran, and alkylating the resulting 4-lithiomethyl-5, 6 or 7-$R_2$-saccharin with the appropriate alkyl halide. Both reactions are carried out at a temperature in the range from $-80°$ C. to $-50°$ C. The above-described 2-$R_1$-3, 4 or 5-$R_2$-N,N-di-lower-alkylbenzamide wherein $R_1$ is primary or secondary alkyl of two to four carbon atoms can be prepared by a similar lithiation-alkylation sequence starting with the corresponding 2-methyl, ethyl or propyl-3, 4 or 5-$R_2$-N,N-di-lower-alkylbenzamide.

A compound of Formula IV wherein $R_1$ is primary or secondary alkyl of two to four carbon atoms can also be prepared by introducing $R_1$ earlier in the synthesis. Conjugate addition of the appropriate $R_1$-cuprate to 2-cyclohexenone and methoxycarbonylation of the resulting copper enolate with methyl cyanoformate by the method of Winkler et al. (Tetrahedron Letters, p. 1051, 1987; Journal of Organic Chemistry, vol. 54, p. 4491, 1989) gives the corresponding 2-methoxycarbonyl-3-$R_1$-cyclohexanone, enol etherification of which with benzylthiol and acidic clay gives a mixture of the corresponding 6-$R_1$-2-benzylthio-1-cyclohexenecarboxylic acid methyl ester and 6-$R_1$-2-benzylthio-3-cyclohexenecarboxylic acid methyl ester, aromatization of which with dichlorodicyanobenzoquinone gives the corresponding 2-$R_1$-6-benzylthiobenzoic acid methyl ester, oxidation-chlorination-benzylation of which with chlorine in aqueous acetic acid gives 2-$R_1$-6-chlorosulfonylbenzoic acid methyl ester, cyclization of which with ammonia gives the corresponding 4-$R_1$-saccharin of Formula IV.

Preparation of certain compounds of Formula IV requires building up both rings thereof. For example, to prepare a compound of Formula IV wherein $R_1$ is lower-alkoxy and $R_2$ is hydroxy, 3,3-thiobispropionic acid is converted with thionyl chloride into the bis acid chloride, which is converted with benzylamine into the bis benzylamide, which on cyclization with sulfuryl chloride gives 5-chloro-2-benzyl-2H-isothiazol-3-one, which on oxidation with one molar equivalent of a peracid gives 5-chloro-2-benzyl-2H-isothiazol-3-one-1-oxide, which on heating under pressure with a 2-lower-alkoxyfuran gives a 4-lower-alkoxy-7-hydroxy-2-benzyl-1,2benzoisothiazol-2H-3-one-1-oxide, which on oxidation with one molar equivalent of a peracid gives the corresponding 4-lower-alkoxy-7-hydroxy-2-benzyl-1,2-benzoisothiazol-2H-3-one-1,1-dioxide, which on debenzylation by catalytic hydrogenation gives the corresponding 4-lower-alkoxy-7-hydroxysaccharin of Formula IV. Alkylation of a thus prepared 4-lower-alkoxy-7-hydroxy-2-benzyl-1,2-benzoisothiazol-2-H-3-one-1-oxide with a lower-alkyl halide or an appropriately substituted lower-alkyl halide followed by oxidation and debenzylation similarly affords the corresponding 4-lower-alkoxy-7-$R_2$-saccharin of Formula IV wherein $R_2$ is lower-alkoxy, cycloalkoxy, B=N-lower-alkoxy, hydroxy-lower-alkoxy, polyhydroxy-lower-alkoxy or acetal or ketal thereof, lower-alkoxy-lower-alkoxy, poly-lower-alkoxy-lower-alkoxy, hydroxy-poly-lower-alkylenoxy or lower-alkoxy-poly-lower-alkylenoxy.

Simple chemical transformations which are conventional and well known to those skilled in the art of chemistry can be used for effecting changes in the functional groups of the compounds of the invention. For example, catalytic reduction of a heterocyclic ring system to produce the corresponding partially saturated heterocyclic ring system, catalytic debenzylation of benzyl ethers to produce the corresponding alcohols, coupling of alcohols with acids in the presence of a coupling agent to produce the corresponding esters, or desilylation of silyl ethers to produce the corresponding alcohols.

The pharmaceutically acceptable acid addition salt can be any pharmaceutically acceptable acid addition salt but preferably has a common anion, for example the hydrochloride salt. If the salt having a common anion is unacceptable because it is not crystalline or insufficiently soluble or hygroscopic, a salt having a less common anion, for example the methanesulfonate, can be used. In any event for use in a mammal the acid addition salt must be nontoxic and must not interfere with the elastase inhibitory effect of the free base form of the compound of Formula I.

The pharmaceutically acceptable base addition salt can be any pharmaceutically acceptable base addition salt but preferably has a common cation, for example the sodium or potassium salt. If the salt having a common cation is unacceptable because it is not crystalline or insufficiently soluble or hygroscopic, a salt having a less common cation, for example the diethylammonium salt, can be used. In any event for use in a mammal the base addition salt must be nontoxic and must not interfere with the elastase inhibitory effect of the free acid form of the compound of Formula I.

In the preparations and examples described below structures of products are inferred from known structures of starting materials and expected courses of preparative reactions. Purification or purity and structural confirmation of starting materials and products were carried out or measured by melting temperature range, optical rotation, elemental analysis, infrared spectral analysis, ultraviolet spectral analysis, mass spectral analysis, nuclear magnetic resonance spectral analysis, gas chromatography, column chromatography, high pressure liquid chromatography, medium pressure liquid chromatography and/or thin layer chromatography.

Preparation of 2-Chloromethyl-4-isopropylsaccharin n-Butyllithium (2.5M, 100 mL) was added with stirring under nitrogen at 0°-5° C. during ten minutes to a solution of 2-isopropylbromobenzene in anhydrous ether (500 mL). The mixture was allowed to warm to room temperature, stirred at room temperature for six hours, and cooled to −60° C. A solution of diethylcarbamyl chloride (34 g) in anhydrous ether (50 mL) was added during 20 minutes while maintaining the temperature below −50° C. The temperature was allowed to rise to room temperature during one hour. Water (100 mL) was added. The ether layer was washed with saturated aqueous solution chloride (200 mL), dried over magnesium sulfate and stripped of ether. Distillation of the residue (80°-90° C./0.1 mm Hg) gave 2-isopropyl-N,N-diethylbenzamide (44 g, 80% yield).

To a solution of N,N,N',N'-tetramethylethylenediamide (25.5 g) in anhydrous ether (600 mL) was added s-butyllithium (1.3M, 170 mL) and the mixture was cooled to −70° C. under nitrogen. A solution of 2-isopropyl-N,N-diethylbenzamide (44 g) in anhydrous ether (300 mL) was added dropwise over 20 minutes. The temperature was maintained at or below −60° C. during the addition. After the addition the mixture was stirred at −70° C. for 30 minutes, allowed to warm to −50° C. during 30 minutes, held at −50° C. for 10 minutes, then cooled back to −70° C. By cannulation tube a solution of sulfur dioxide (50 g) in anhydrous ether (50 mL) precooled to −60° C. was added under positive nitrogen pressure over a 10-minute period. The temperature of the reaction mixture during the addition was maintained below −50° C. A white powdery precipitate of aryllithium sulphinate separated out almost immediately. The temperature was allowed to rise to room temperature during one hour. Sulfuryl chloride (54 g) was added dropwise with continued stirring during 15 minutes. After further stirring for 30 minutes at 0°-5° C. a white precipitate was filtered off and washed with anhydrous ether (2 L). Removal of the solvent under vacuum gave a faint yellow oil, which was dissolved in tetrahydrofuran (150 mL). The solution was cooled to 0° C. and concentrated aqueous ammonia (28%, 60 mL) was added in portions over 15 minutes. The temperature was kept at 10° C. or below throughout the addition. After stirring for 15 minutes at ambient temperature the tetrahydrofuran and excess ammonia were removed and the residue was acidified with hydrochloric acid (2N) to pH 1. The resulting white solid was collected, washed with water (200 mL) and hexane (200 mL) and dried affording 2-aminosulfonyl-6-isopropyl-N,N-diethylbenzamide (54 g, 90% yield).

A solution of 2-aminosulfonyl-6-isopropyl-N,N-diethylbenzamide (60 g) in acetic acid (400 mL) was refluxed for 24 hours, then cooled to room temperature. The solvent was removed under vacuum. The oily residue was dissolved in water (500 mL) and the pH was adjusted to 1 with hydrochloric acid (2N). The crude product was collected by filtration, washed with water (300 mL), dried at 60° C. under vacuum for 18 hours and recrystallized from ether-hexane to give 4-isopropylsaccharin (40 g, 90% yield, m.p. 177° C.).

A mixture of 4-isopropylsaccharin (37.9 g), phenyl chloromethyl sulfide (33.3 g), tetrabutylammonium bromide (5.4 g) and toluene (200 mL) was heated under reflux for 24 hours, then stripped of volatiles. Column chromatography of the residue on silica gel (485 g) and elution first with hexane, then hexane-dichloromethane (1:1), then dichloromethane gave in the hexane-dichloromethane eluate 2-phenylthiomethyl-4,-isopropylsaccharin as a pale yellow oil (53.5 g, 92% yield).

2-Phenylthiomethyl-4-isopropylsaccharin (53.5 g), sulfuryl chloride (40 mL, 67.2 g) and dichloromethane (250 mL) were mixed with stirring at room temperature. The mixture underwent a slightly exothermic reaction and was allowed to stand for 17 hours at room temperature, then stripped of volatiles. The residue crystallized with hexane in three crops (33.65 g, m.r. 101°-102° C.; 3.45 g, m.r. 100°-101° C.; 0.45 g, m.r. 99°-100° C.; total 38.55 g, 91% yield). The three crops were combined and recrystallized from isopropyl alcohol (30 mL)-cyclohexane (270 mL) affording 2-chloromethyl-4-isopropylsaccharin in two crops (33.5 g, m.r. 101°-102.5° C.; 2.65 g, m.r. 100°-101° C.).

Preparation of
2-Chloromethyl-4-isopropyl-6-methoxysaccharin

To a solution of N,N,N',N'-tetramethylethylenediamine (300 mL) in anhydrous ether (4 L) was added s-butyllithium (1.3M, 4 L) and the mixture was cooled in −70° C. under nitrogen. A solution of 2-isopropyl-4-methoxy-N,N-diethylbenzamide (454.2 g) in anhydrous ether (300 mL) was added dropwise over 30 minutes. The temperature was maintained at or below −60° C. during the addition. After the addition the mixture was stirred at −70° C. for one hour, allowed to warm to −50° C. for 30 minutes, then cooled back to −70° C. By cannulation tube a solution of sulfur dioxide (200 g) in anhydrous ether (200 mL) precooled to −40° C. was added under positive nitrogen pressure over a 20-minute period. The temperature of the reaction mixture during the addition was maintained below −40° C. A white powdery precipitate of aryllithium sulphinate separated out almost immediately. After the addition the cooling bath was removed and the mixture was stirred at ambient temperature for two hours, then cooled to −5° C. With continued stirring sulfuryl chloride (190 mL) was added dropwise over a 15-minute period while maintaining the temperature below 10° C. After further stirring for 30 minutes at 0°–5° C. a white precipitate was filtered off and washed with anhydrous ether (2 L). Removal of the solvent at atmospheric pressure gave a dark oil, which was dissolved in tetrahydrofuran (1.4 L). The solution was cooled to −10° C. and concentrated aqueous ammonia (28%, 540 mL) was added in portions over 15 minutes. The temperature was kept at 15° C. or below throughout the addition. After stirring for 15 minutes at ambient temperature the tetrahydrofuran and excess ammonia were removed under vacuum to give a dark oil, which was diluted with water (6.0 L) and acidified with hydrochloric acid (3N) to pH 1. The resulting light yellow solid was collected by filtration, washed with water (800 mL), dried at 60° C. under vacuum for 18 hours and recrystallized from ethyl acetate-hexane (800 mL-3 L) to give 2-aminosulfonyl-6-isopropyl-4-methoxy-N,N-diethylbenzamide (429 g, 72% yield, m.r. 122°–125° C.).

A solution of 2-aminosulfonyl-6-isopropyl-4-methoxy-N,N-diethylbenzamide (429.6 g) in acetic acid (1.5 L) was refluxed for 20 hours, then cooled to room temperature. The solvent was removed under vacuum. The oily residue was dissolved in water (6 L) and the pH was adjusted to 1 with hydrochloric acid (6N). The crude product was collected by filtration, washed with water (2 L), dried at 60° C. under vacuum for 18 hours and recrystallized from ethyl acetate-hexane to give 4-isopropyl-6-methoxysaccharin (303 g, 91% yield, m.p. 188° C.).

To ba suspension of paraformaldehyde (24 g) and chlorotrimethylsilane (86.4 g) in 1,2-dichloroethane (200 mL) was added dry tin(IV) chloride (0.8 mL) and the resulting solution was stirred on a steam bath for one hour. 4-Isopropyl-6-methoxysaccharin (51.4 g) was added to the clear solution and the mixture was refluxed for 18 hours, cooled to room temperature and poured into water. The organic layer was separated, washed with aqueous sodium hydroxide solution (2N, 50 mL), dried over magnesium sulfate and concentrated under vacuum. The residue was crystallized from ethyl acetate-hexane to give 2-chloromethyl-4-isopropyl-6-methoxysaccharin (57 g, 87% yield, m.p. 151° C.).

Preparation of 2-chloromethyl-4-isopropyl-6-[2-(benzyloxy)ethoxy]saccharin

To a solution of 1.0 g (0.0039 mol) of 4-isopropyl-6-methoxysaccharin in 15 ml of MDC was added at ambient temperature 1.28 g (5.12 ml) of a 1M solution of boron tribromide in MDC. When addition was complete the reaction mixture was heated under reflux for about five hours, cooled, taken to dryness in vacuo and the residue treated with ice and saturated sodium bicarbonate. The aqueous solution was extracted once with ethyl acetate and then acidified to pH 1 with concentrated hydrochloric acid. Extraction of the mixture with ethyl acetate/diethyl ether (8:2), drying the organic extracts and removal of the solvent in vacuo afforded 0.9 g (96%) of 6-hydroxy-4-isopropylsaccharin as a white crystalline solid which was used as such in the next step.

An alternative procedure was also used. To a stirred suspension of 62.74 g (0.47 mol) of $AlCl_3$ in 500 mL of chloroform at 0° C. was added 43.9 g (0.7 mol) of ethanethiol. Within minutes a clear solution formed. To this a solution of 20.0 g (0.078 mol) of 4-isopropyl-6-methoxysaccharin in 550 mL of chloroform was added over a 30-min period. This solution was allowed to warm to RT and stirred for 3–4 hrs. at 60° C. After cooling, the mixture was poured into ice-water and acidified with dilute HCl. The solid which separated was collected by filtration, washed with water and dried to give 18.4 g (97%) of 6-hydroxy-4-isopropylsaccharin.

6-hydroxy-4-isopropylsaccharin (30.0 g, 0.12 mol) in methanol was treated with $Cs_2CO_3$ (20.28 g, 0.062 mol). The mixture was stirred at ambient temperature for 3–4 hours, the excess methanol was removed under reduced pressure and the residue was dried under high vacuum. The residue was dissolved in DMF and chloromethyl phenyl sulfide (21.72 g, 0.14 mol) was added. The mixture was heated at 70°–80° C. for 24 hours, cooled, treated with ice-water and extracted with ethyl acetate/ether. The organic layer was washed with water, then brine and was dried. The solvent was removed in vacuo and the residue was purified by column chromatography on silica eluting with ethyl acetate/hexane to afford 30.5 g (67%) of 4-isopropyl-6-hydroxy-2-phenylthiomethylsaccharin.

To a solution of 6-hydroxy-4-isopropyl-2-phenylthiomethylsaccharin (2.0 g, 5.5 mol) in THF (40 mL) were added triphenylphosphine (1.46 g, 5.56 mmol), 2-benzyloxyethanol (0.87 g, 5.71 mmol) and triphenylphosphine (0.99 g, 5.68 mmol). The mixture was stirred at room temperature for 16 hours, the solvent was removed in vacuo and the residue was purified by column chromatography on silica eluting with 20% EtOAc/hexane to afford 2.1 g (77%) of 4-isopropyl-6-[2-(benzyloxy)ethoxy]-2-phenylthiomethylsaccharin, m.p. 98°–99° C.

Sulfuryl chloride (0.37 mL, 4.65 mmol) was added to a solution of the latter (2.1 g, 4.22 mmol) in $CH_2Cl_2$ at room temperature and the mixture was stirred for 3 hours. The solvent was removed in vacuo, the residue was triturated with hexane, and the solid thus formed was collected by filtration to afford 1.67 g (93%) of 2-chloromethyl-4-isopropyl-6-[2-(benzyloxy)ethoxy]saccharin, m.p. 101°–102° C.

Preparation of 2-chloromethyl-4-isopropyl-6-[2-(triisopropylsilyloxy)ethoxy]saccharin To a solution of 4-isopropyl-6-hydroxy-2-phenylthiomethylsaccharin. (2.0 g, 5.509 mmol) in THF (35 mL) containing triphenylphosphine (1.59 g, 6.06 mmol) and 2-(triisopropylsilyloxy) ethanol (1.13 g, 6.0 mmol) at room temperature was added diethylazodicarboxylate (1.04 mL, 6.6 mmol). The mixture was stirred overnight (16 hours), the solvent was removed in vacuo and the residue was purified by column chromatography on silica eluting with 10% ethyl acetate/hexane to afford 2.66 g (86%) of 4-isopropyl-6-[2-(triisopropylsilyloxy)ethoxy]-2-phenylthiomethylsaccharin as an oil.

The latter (2.6 g, 4.62 mmol) in $CH_2Cl_2$ (30 mL) was treated with sulfuryl chloride (0.65 g, 4.51 mmol) and the mixture was stirred for 3 hours. The solvent was removed in vacuo, and the residue was triturated with hexane. The product was collected by filtration to afford 1.73 g (76%) or 2-chloromethyl-4-isopropyl-6-[2-(triisopropylsilyloxy)ethoxy]saccharin, m.p. 85°–86° C.

Preparation of 2-chloromethyl-4-isopropyl-6-(benzyloxycarbonylmethoxy)saccharin A mixture of 4-isopropyl-6-hydroxy-2-phenylthiomethyl-saccharin (3.5 g, 9.63 mmol), acetone (25 mL) and $K_2CO_3$ (2.66 g, 19.26 mmol) was stirred under nitrogen for 2 minutes, then benzylbromoacetate (2.4 mL, 14.45 mmol) was added. The mixture was stirred for 6 hours, filtered, and the filtrate was concentrated in vacuo. The residue was purified by medium pressure chromatography eluting with 20% ethyl acetate/hexane to afford 4.67 (100%) of 4-isopropyl-6-(benzyloxycarbonylmethoxy)-2-phenylthiomethylsaccharin.

To a solution of the latter (0.5 g 1.043 mmol) in $CH_2Cl_2$ (5 mL) at room temperature was added sulfuryl chloride. The mixture was stirred for 4 hours, the solvent was removed in vacuo and the residue was purified by column chromatography on silica eluting with hexane (100%) to 20% ethyl acetate/hexane to afford 0.37 g (81%) of 2-chloromethyl-4-isopropyl-6-(benzyloxycarbonylmethoxy)saccharin.

Preparation of 2-chloromethyl-4-isopropyl-6-hydroxysaccharin 4-isopropyl-6-hydroxy-2-phenylthiomethylsaccharin (1.78 g) in methylene chloride was treated with sulfuryl chloride (0.43 mL, 0.73 g) to afford 1.2 g 84%) of 2-chloromethyl-4-isopropyl-6-hydroxysaccharin, m.p. 149°–150° C.

Preparation of 2-chloromethyl-4-sec-butyl-6-methoxysaccharin

To a mixture of diethylamine (89.1 mL), triethylamine (120.2 mL) and $CH_2Cl_2$ (500 mL) cooled in an icebath was added dropwise p-anisoyl chloride (133.8 g) over 40 minutes. The reaction mixture was stirred at room temperature for 40 minutes, the mixture was filtered, washed with ether and the solvent was removed in vacuo. Ether was added, then water to the residue, then the organic layer was separate and washed with 5% NaOH, then in HCl, then brine and then was dried over $Na_2SO_4$. The solvent was removed in vacuo and the residue was purified by kugelrohr distillation at 140°–180° C. under high vacuum to afford 163.8 g of 4-methoxy-N,N-diethylbenzamide, m.p. 40°–42° C.

To a solution of tetramethylethylenediamine (50.3 mL) in THF (800 mL) at −78° C. was added sec-BuLi (308 mL, 1.08M), followed by 4-methoxy-N,N-diethylbenzamide, (62.2 g). The mixture was stirred at −78° C. for 70 minutes, then ethyliodide (26.63 g, 333 mmol) was added over 35 minutes. The reaction mixture was warmed to room temperature and stirred for 1.5 hours. The reaction mixture was quenched with saturated $NH_4Cl$ (100 mL). The organic layer was separated, dried over $Na_2SO_4$ and concentrated in vacuo. The residue was purified by a kugelrohr distillation at 190°–210° C. under high vacuum to afford 58.1 g of 2-ethyl-4-methoxy-N,N-diethylbenzamide.

To a mixture of diisopropylamine (40.7 mL, 290 mmol) in THF (800 mL) at −78° C. was added n-BuLi (100 ML, 255 mmol, 2.15M). The mixture was stirred for ¼ hour, then 2-ethyl-4-methoxy-N,N-diethylbenzamide (235.3 g) in THF (300 mL) was added at −78° C. The mixture was stirred at −78° C. for 2.5 hours, then at 0° C. for 1 hour, and then ethyliodide (23.2 mL) in THF (150 mL) was added over 10 minutes at −78° C. The reaction mixture was stirred for about 1 hour, quenched with saturated $NH_4Cl$ (100 mL) and the solvent was removed in vacuo. Ether (500 mL) was added to the residue, the ether layer was washed with saturated $NaHCO_3$ (50 mL), 1N HCl (50 mL), water, then brine, and then the ether layer was dried over $Na_2SO_4$ and the solvent was removed in vacuo. The residue was purified by distillation under high vacuum (2 mm Hg) to afford 46.6 g (76%) of 2-sec-butyl-4-methoxy-N,N-diethylbenzamide.

To a solution of tetramethylethylenediamine (31 mL) in THF (500 mL) at −78° C. was added sec-butyllithium (170 mL, 1.1M), followed by 2-sec-butyl-4-methoxy-N,N-diethylbenzamide (45 g) in THF (150 mL). The mixture was stirred at −78° for 15 minutes, then at 0° C. for 30 minutes, then sulfur dioxide (50 mL) was condensed into the mixture at −78° C. The mixture was warmed to −10° C., sulfuryl chloride (17 mL) was added and then the mixture was slowly warmed to room temperature and stirred overnight. The reaction mixture was added to a solution of ammonium hydroxide (94 mL) in THF (200 mL), the mixture was filtered through a pad of silica/$Na_2SO_4$/sand to afford 51.8 g of 2-aminosulfonyl-6sec-butyl-4-methoxy-N,N-diethylbenzamide.

A mixture of acetic acid (200 mL) and 2-aminosulfonyl-6-sec-butyl-4-methox-N,N-diethylbenzamide (51.7 g) was refluxed overnight. The acetic acid was removed by distillation, the residue was poured into ice/2M NaOH (80 mL). The aqueous solution was washed with $CH_2Cl_2$, acidified with concentrated HCl and the precipitate which formed was collected by filtration to afford 4-sec-butyl-6-methoxysaccharin.

A mixture of 4-sec-butyl-6-methoxysaccharin (3 g), toluene, potassium t-butoxide (1.4 g), and tetrabutylammonium bromide (0.4 g) was brought to reflux and phenylchloromethyl sulfide (1.8 mL) was added. The reaction mixture was refluxed for about 27 hours, the solvent was removed in vacuo, the reside was extracted with ethyl acetate, washed with brine and dried over $Na_2SO_4$. The solvent was removed in vacuo and the residue was purified by column chromatography on silica eluting with 10% ethyl acetate/hexane to afford 2.63 g (60%) of 2-phenylthiomethyl-4-sec-butyl-6-methoxysaccharin.

To a solution of 2-phenylthiomethyl-4-sec-butyl-6-methoxysaccharin (2.6 g) in $CH_2Cl_2$ (20 mL) was added sulfuryl chloride (0.7 mL). The mixture was stirred at ambient temperature overnight, and the solvent was removed in vacuo. The residue was treated with hexane and the mixture was sonicated for 6 hours. A precipitate formed with a collected by filtration to afford 1.33 g of 2-chloromethyl-4-sec-butyl-6-methoxysaccharin.

Preparation of 2-chloromethyl-4-sec-butylsaccharin

To a solution of 4.74 mL (0.031 mol) of tetramethylethylenediamine in 300 mL of THF (passed through alumina prior to use) was added 5.8 g (0.03 mol) of 2-ethyl-N,N-diethyl-benzamide. The solution was cooled to −78° C. and treated with 34.9 mL (0.031 mol) of a 0.9M solution of butyl lithium in cyclohexane. When addition was completed, the mixture was stirred for twenty minutes and then treated with a solution of 3.2 mL (0.04 mol) of ethyliodide while maintaining the temperature at −78° C. The temperature was then allowed to rise to ambient temperature and the mixture was stirred for about sixteen hours and then poured into water. The resulting oil was separated and chromatographed on silica gel, eluting with 10% ethyl acetate/hexane to give 2.86 g (43%) of 2-sec-butyl-N,N-diethyl-benzamide as yellow oil.

The latter (10.45 g, 0.045 mol), dissolved in 70 mL of THF, was added to a solution of 39.2 mL (0.047 mol) of a 1.2M solution of s-butyl lithium in cyclohexane and 7.1 mL (0.047 mol) of tetramethylethylenediamine in 250 mL of THF while maintaining the temperature at −78° C. When addition was complete, the mixture was stirred for an additional one half hour at −78° C. and then treated with sulfur dioxide at −70° C. and then allowed to warm to room temperature. The mixture was taken to dryness in vacuo, and the residue was dissolved in water and added with stirring to a cold solution of 15.2 g (0.134 mol) of hydroxylamine-O-sulfonic acid and 15.4 mL (0.134 mol) of 35% sodium hydroxide to give 10.1 g (72%) of 2-aminosulfonyl-6-sec.-butyl-N,N-diethylbenzamide.

The latter (6.83 g, 0.22 mol) was dissolved in 100 mL of glacial acetic acid and the solution heated under reflux for thirteen hours and then taken to dryness. The residue was triturated with diethyl ether and collected by filtration to give 5.7 g (83%) of the diethylammonium salt of 4-sec.-butylsaccharin.

The latter (3.0 g, 0.0096 mol), on reaction with 1.13 mL (0.012 mol) of chloromethyl phenyl sulfide in toluene, afforded 3.47 g (100%) of 2-phenylthiomethyl-4-sec.-butylsaccharin.

Reaction of the latter (3.2 g, 0.00097 mol) with 2.3 mL (0.029 mol) of sulfuryl chloride in 20 mL of methylene chloride afforded 2.4 g (87%) of 2-chloromethyl-4-sec.-butylsaccharin.

The following examples of compounds of Formula I were prepared.

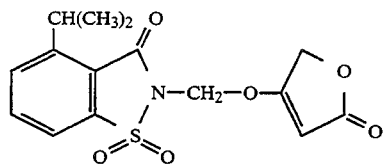

A solution of tetronic acid (0.22 g) in dimethylformamide (5 mL) was added to a suspension of sodium hydride (60% dispersion in mineral oil, 0.10 g) in dimethylformamide (4 mL) under nitrogen with stirring and ice-bath cooling. The ice bath was removed, stirring was continued for 15 minutes, a solution of 2-chloromethyl-4-isopropylsaccharin (0.547 g) in dimethylformamide (10 mL) was added dropwise, stirring was continued for two and one-half days, and the mixture was poured into water. The resulting mixture was extracted with ethyl acetate. The ethyl acetate layer was dried over magnesium sulfate and stripped of ethyl acetate. Recrystallization of the resulting colorless solid (0.60 g) from ethyl acetate gave 2-[(2,5-dihydro-5-oxo-3-furanyl)oxymethyl]-4-isopropylsaccharin (0.34 g, 51% yield, m.r. 174°–175° C.).

EXAMPLES 1B–1W

By methods similar to that of Example 1A above the compounds identified in Table I below were prepared from 2-chloromethyl-4-isopropylsaccharin or 2-chloromethyl-4-isopropyl-6-methoxysaccharin and the corresponding compound of Formula III (H—O—Z).

TABLE I

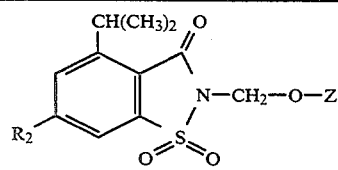

| Example | R₂ | —Z | Yield (%) Melting Range (°C.) Recrystallization Solvent |
|---|---|---|---|
| 1B | H | (structure) | 40 229–230 Ethyl acetate |

TABLE I-continued

[Structure: isopropyl-substituted benzene ring with R₂ substituent, bearing a C(=O)-N(-CH₂-O-Z)-SO₂ group forming a cyclic sulfonamide]

| Example | R₂ | —Z | Yield (%) Melting Range (°C.) Recrystallization Solvent |
|---|---|---|---|
| 1C | H | [N-methyl-2-oxo-dihydroquinolinyl group] | 51<br>185–188<br>Ethanol |
| 1D | H | [6-methyl-2-oxo-2H-pyran-4-yl group] | 58<br>188–189.5<br>Ethanol-hexane |
| 1E | H | [3-(C₆H₅CO)-4-methyl-6-methyl-2-oxo-2H-pyran group] | 13<br>204–207<br>Ethanol |
| 1F | H | [6-phenyl-2-oxo-2H-pyran-4-yl group] | 18<br>178–189.5<br>Isopropyl alcohol |
| 1G | CH₃O | [6-methyl-2-oxo-2H-pyran-4-yl group] | 50<br>172.5–174<br>Ethyl acetate |
| 1H | CH₃O | [3-(C₆H₅CO)-6-methyl-2-oxo-2H-pyran group] | 24<br>175–177<br>Ethanol |
| 1I | CH₃O | [CH₃-substituted pyrido-pyranone group] | 42<br>165.5–167.5<br>Ethyl acetate |

TABLE I-continued

[Structure: isopropyl-substituted benzene with R₂, sulfonyl, and N-CH₂-O-Z carboxamide group]

| Example | R₂ | —Z | Yield (%) Melting Range (°C.) Recrystallization Solvent |
|---|---|---|---|
| 1J | CH₃O | 1-methyl-6-methyl-2-pyridinone | 34<br>168–170<br>Ethyl acetate |
| 1K | CH₃O | 3-benzyl-4-methyl-2(5H)-furanone | 47<br>126.5–128.5<br>Ethyl acetate |
| 1L | CH₃O | 4-methylcoumarin | 39<br>261.5–263<br>Ethyl acetate |
| 1M* | CH₃O | 2,3-dimethyl-2-cyclohexenone | 6<br>129–131<br>Ethyl acetate-cyclohexane |
| 1N | CH₃O | 4-methyl-2(5H)-furanone | 33<br>195–196.5<br>Ethyl acetate |
| 1O | CH₃O | 3-benzyl-4-methyl-5-(2-methylpropyl)... | 48<br>136.5–137.5<br>Carbon tetrachloride |
| 1P | CH₃O | 3-(morpholinomethyl)-4-methyl-2(5H)-furanone | 8<br>145–147<br>Ethyl acetate-cyclohexane |

TABLE I-continued

[Structure: Substituted saccharin derivative with CH(CH3)2 at one position, R2 at another, and N—CH2—O—Z group on the sulfonamide nitrogen]

| Example | R2 | —Z | Yield (%) Melting Range (°C.) Recrystallization Solvent |
|---|---|---|---|
| 1Q | CH3O | 2-methyl-3-oxocyclopent-1-enyl (with CH3) | 32<br>115–117<br>Carbon tetrachloride |
| 1R | CH3O | 2-chloro-3-oxo group with O | 29<br>149.5–150.5<br>Carbon tetrachloride |
| 1S | CH3O | thiochromen-2-one group | 29<br>227–228<br>Methanol |
| 1T | CH3O | 3-methyl-1-oxo-1H-indene | 7.7<br>193–203 (dec.)<br>Benzene/hexane[a] |
| 1U | CH3O | 2-(morpholinomethyl)-4,4-dimethyl-3-methyl-cyclopent-2-enone | 22.5<br>Foam<br>(b) |
| 1V | CH3O | 3-methyl-2-oxocyclobut-3-enyl | 23<br>129–132 (dec.)<br>(c) |
| 1W | CH3O | 2-benzyl-3-methyl-cyclopent-2-enone | 36<br>122.5–124<br>Benzene/hexane[d] |

[a]Product was purified by column chromatography on silica eluting with CH2Cl2, followed by varying amounts of ethyl acetate/hexane prior to recrystallization.
(b) Product was purified by column chromatography on silica eluting with CH2Cl2, followed by ethyl acetate/hexane in varying amounts.
(c) Product was purified by column chromatography (2×) on silica eluting with CH2Cl2, followed by varying amounts of ethyl acetate/hexane.
[d]Product was purified by column chromatography on silica eluting with ethyl acetate/hexane (⅓ to ½).
*In addition to the compound of Formula I of Example 1M 2-(1-methyl-2,6-dioxocyclohexyl)methyl-4-isopropyl-6-methoxysaccharin (m.r. 159.5–161.5° C. from ethyl acetate) was isolated in 38% yield.

EXAMPLE 2

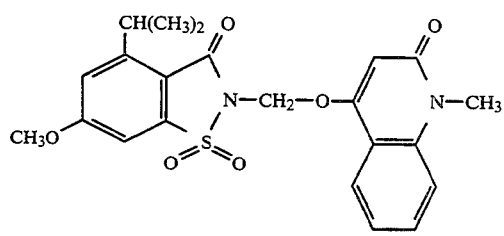

4-Hydroxy-1-methylcarbostyryl (1.44 g) was added with stirring to a suspension of sodium hydride (60% dispersion in mineral oil, 0.36 g) in dimethylformamide. The mixture was heated at 100° C. with continued stirring for three-fourths hour, then sonicated at room temperature for one-half hour. 2-Chloromethyl-4-isopropyl-6-methoxysaccharin (1.83 g) was added. The resulting mixture was heated at 100° C. with continued stirring for two hours, then poured into water (300 mL). Hydrochloric acid (1N, 25 mL) was added, and the mixture was extracted with chloroform. The chloroform extract was dried over sodium sulfate and stripped of chloroform. Flash chromatography of the resulting solid (3.3 g) on silica gel using ethyl acetate-hexane (1:1) as eluant and recrystallization of the resulting solid (0.7 g, 28% yield) from ethanol (90%) gave 2-(1-methylcarbostyryl-4-yl)oxymethyl-4-isopropyl-6-methoxysaccharin as a yellow solid (0.39 g, 15% yield, m.r. 198°–200° C.).

EXAMPLE 3A

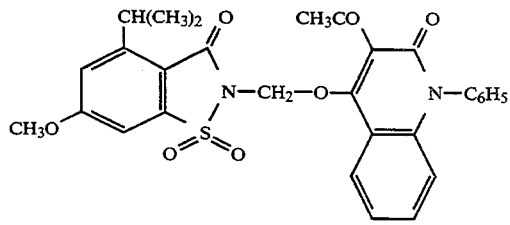

A mixture of 3-acetyl-4-hydroxy-1-phenylcarbostyril (0.52 g), potassium carbonate (0.28 g) and dimethylformamide (7 mL) was stirred at room temperature for one-half hour. 2-Chloromethyl-4-isopropyl-6-methoxysaccharin (0.71 g) was added and the mixture was sonicated for one hour at 40° C. and stirred at room temperature for 16 hours. Further sonication did not change the extent of reaction as shown by thin layer chromatography. The reaction mixture was poured into water and the mixture was extracted with ethyl acetate. The ethyl acetate extract was dried and stripped of ethyl acetate. Medium pressure liquid chromatography of the residue (0.5 g) on silica gel using ethyl acetate-hexane (3:7) as eluant and recrystallization of the product from methanol gave 2-(1-phenyl-3-acetylcarbostyryl-4-yl)oxymethyl-4-isopropyl-6-methoxysaccharin (0.24 g, 24% yield, m.r. 210°–212° C.

EXAMPLE 3B

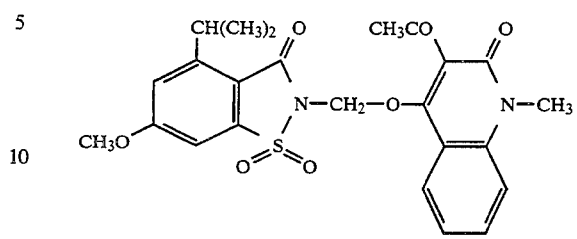

By a method similar to that of Example 3A above 3-acetyl-4-hydroxy-1-methylcarbostyryl (0.63 g) was condensed with 2-chloromethyl-4-isopropyl-6-methoxysaccharin (1.10 g) and the product was purified by crystallization from methanol-ether to give 2-(1-methyl-3-acetylcarbostyryl-4-yl)oxymethyl-4-isopropyl-6-methoxysaccharin as an off-white power (0.28 g, 20% yield, m.r. 194°–196° C.).

EXAMPLE 4A

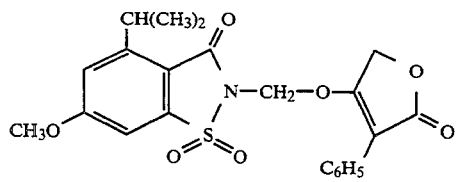

Cesium carbonate (0.82 g) was added to a solution of 3-phenyl-2(5H)-furanone (0.88 g) in methanol (15 mL) and the mixture was stirred at room temperature for one hour and stripped of methanol. 2-Chloromethyl-4-isopropyl-6-methoxysaccharin (1.52 g) was added to a solution of the residue in dimethylformamide (15 mL) and the mixture was stirred at room temperature for two days. Silica gel (4.4 g) was added, volatiles were removed under vacuum, and the solid was subjected to flash chromatography on silica gel using ethyl acetate-hexane (3:7) as eluant. Recrystallization of the product from ethanol-ether gave 2-(2,5-dihydro-2-oxo-3-phenyl-furan-4-yl)oxymethyl-4-isopropyl-6-methoxysaccharin as a colorless solid (0.45 g, 20% yield, m.r. 180°–182° C.).

EXAMPLES 4B–4I

By methods similar to that of Example 4A above the compounds identified in Table II below were prepared from 2-chloromethyl-4-isopropyl-6-methoxysaccharin and the corresponding compound of Formula III (H—O—Z).

TABLE II

[Structure: saccharin derivative with CH(CH₃)₂, CH₃O, and N—CH₂—O—Z substituents]

| Example | —Z | Yield (%)/Melting Range (°C.) Recrystallization Solvent |
|---|---|---|
| 4B | C₆H₅CH₂ | 46/204–206 Dichloromethane-ether |
| 4C | [pyrido[1,2-a]pyrimidin-4-one-2-yl] | 61/173–176 Methanol |
| 4D | [3-chloro-pyrido[1,2-a]pyrimidin-4-one-2-yl] | 9/225–227 Methanol-dichloromethane |
| 4E | [6,6-dimethyl-4-oxo-4H-pyran-2-yl] | 58/141–142.5 None |
| 4F | [1-phenyl-3-phenoxy-pyrrolin-2-one-5-yl] | 51/85–87 None |
| 4G | [1-phenyl-3-piperidino-pyrrolin-2-one-5-yl] | 19/83–88 None |
| 4H | [pyrido[1,2-a]pyrazin-4-one-2-yl] | 20.5/133–135 (as monohydrate) EtOH/Water[a] |
| 4I | [6-phenyl-4H-pyran-4-one-2-yl] | 3.9/218–220 (as ¼ hydrate) CH₃CN[b] |

[a] The reaction mixture was worked-up by pouring it into ice/water, extracting with ethyl acetate, washing the organic layer with 5% NAOH, 1N HCl, water and then brine, and then removing the solvent in vacuo. The residue was then purified by column chromatography on silica eluting with 40% ethyl acetate/hexane prior to recrystallization.

(a) The reaction mixture was worked-up by pouring it into ice/water, extracting with ethyl acetate, washing the organic layer with 5% NaOH, 1N HCl, water and then brine, and then removing the solvent in vacuo. The residue was then purified by column chromatography on silica eluting with 40% ethyl acetate/hexane prior to recrystallization.

(b) The reaction mixture was worked-up by pouring it into water, adding 5% NaOH, extracting with EtOAc/CH₂Cl₂, combining the organic layers, washing the organic layers with water then drying it over Na₂SO₄. The solvent was removed in vacuo, and the residue was purified by column chromatography on silica eluting with 25% EtOAc/hexane to EtOAc (100%) prior to recrystallization.

EXAMPLE 4J

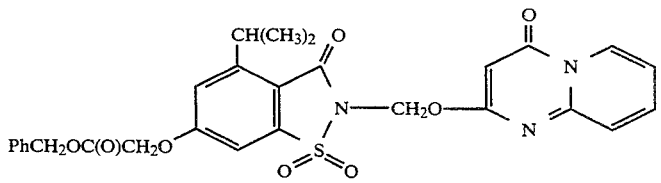

Following a procedure similar to that described in Example 4A, there was prepared 0.71 g (62.8%) of 2-[4-oxo-4H-pyrido[1,2-a]pyrimidin-2-yl]oxymethyl-4-isopropyl-6-(benzyloxycarbonylmethoxy)saccharin, m.p. 69°–71° C., from 2-chloromethyl-4-isopropyl-6-(benzyloxycarbonylmethoxy) saccharin (0.876 g), cesium carbonate (0.326 g), methanol, 2-hydroxypyrido[1,2-a]pyrimidine-4-one (0.324 g), and DMF (5 mL). The reaction mixture was worked-up by pouring it into ice/water, extracting with ethyl acetate, separating out the organic layer and washing the organic layer with brine and then drying it over Na₂SO₄.

EXAMPLE 4K

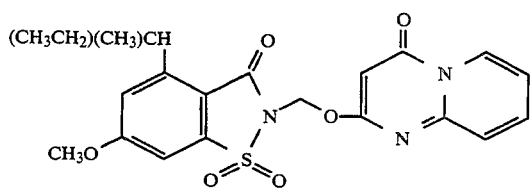

Following a procedure similar to that described in Example 4A, there was prepared 0.267 g (58%) of 2-[4-oxo-4-H-pyrido[1,2-a]pyrimidine-2-yl]oxymethyl-4-sec-butyl-6-methoxysaccharin, m.p. 160°-185° C., from 2-chloromethyl-4-sec-butyl-6-methoxysaccharin (0.318 g, 1.0 mmol), 2-hydroxypyrido [1,2-a]pyrimidine-4-one (0.18 g, 1.11 mmol), cesium carbonate (0.18 g, 0.56 mmol), methanol (5 mL), and DMF. The reaction mixture was worked up by pouring it into saturated ammonium chloride, extracting with ethyl acetate, concentrating the organic layer in vacuo and purifying the residue by column chromatography on silica eluting with 50% ethyl acetate/hexane, followed by 5% methanol/ethyl acetate.

EXAMPLE 5

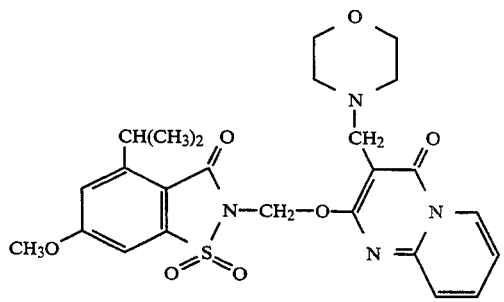

A mixture of 3-(4-morpholinylmethyl)pyrido[1,2-a]pyrimidine-2,4-dione hydrochloride (0.6 g) and potassium t-butoxide (0.49 g) in dimethylformamide (20 mL) was stirred at room temperature for five minutes. 2-Chloromethyl-4-isopropyl-6-methoxysaccharin (0.61 g) was added and stirring was continued at room temperature for one hour. The reaction mixture was diluted with water (50 mL) and extracted with dichlormethane (3×200 mL). The dichloromethane extract was dried over sodium sulfate and stripped of volatiles, finally under high vacuum. The crude product (780 mg) was combined with that (0.65 g) from another run at the same scale using sodium hydride (60% dispersion in mineral oil, 0.19 g) instead of potassium t-butoxide and purified by column chromatography on silica gel with dichloromethane-methanol (95:5) as eluant affording 2-[3-(4-morpholinylmethyl)-4-oxo-4H-pyrido[1,2-a]pyrimidin-2-yl]oxymethyl-4-isopropyl-6-methoxysaccharin (500 mg, 23% yield), part of which was recrystallized from ethanol (m.r. 177°-180° C.).

EXAMPLE 6

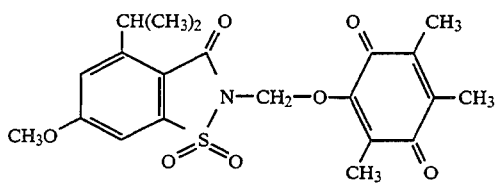

2-Chloromethyl-4-isopropyl-6-methoxysaccharin (0.34 g) was added with stirring at room temperature to a solution of 2-hydroxy-3,5,6-trimethyl-1,4-quinone (0.182 g) and methyltriazabicyclodecene (0.18 g) in acetonitrile (20 mL). Stirring at room temperature was continued for 24 hours and the dark colored solution was poured into ice-water containing a few drops of hydrochloric acid. The resulting tan solid was purified first by column chromatography on silica gel and then recrystallization from hot ethanol affording 2-(3,5,6-trimethyl-1,4-dioxo-2,5-cyclohexadien-2-yl)oxymethyl-4-isopropyl-6-methoxysaccharin (60 mg, 12.7% yield, m.r. 164°-166° C.).

EXAMPLE 7

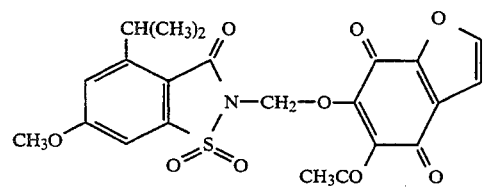

2-Chloromethyl-4-isopropyl-6-methoxysaccharin (0.5 g) was added with stirring at room temperature to a solution of 4,7-dimethoxy-5-acetyl-6-hydroxybenzofuran (0.39 g) and methyltriazabicyclodecene (0.28 g) in acetonitrile (20 mL). The mixture was stirred overnight at room temperature. Since thin layer chromatography showed unreacted 4,7-dimethoxy-5-acetyl-6-hydroxybenzofuran, more 2-chloromethyl-4-isopropyl-6-methoxysaccharin and a drop of base were added, stirring was continued for a total of 24 hours, and the reaction mixture was poured into ice-water containing hydrochloric acid. The resulting golden solid was partially purified using dichloromethane as eluant. The reaction was repeated with stirring overnight at 35°-40° C. instead of room temperature. The product and the partially purified product of the first reaction were combined and purified by column chromatography on silica gel affording 2-(4,7-dimethoxy-5-acetylbenzofuran-6-yl)oxymethyl-4-isopropyl-6-methoxysaccharin (0.4 g, 24% yield).

A solution of triceric tetraammonium hexanitrate (0.98 g) in water (3 mL) was added dropwise to a solution of 2-(4,7-dimethoxy-5-acetylbenzofuran-6-yl)oxymethyl-4-isopropyl-6-methoxysaccharin (0.3 g) in acetonitrile (5 mL). The mixture was stirred at room temperature for 15 minutes and poured into ice-water. The resulting gold colored solid was purified by rapid chromatography on silica gel with dichloromethane-ether (95:5) as eluant and crystallization with sonication from ethanol affording 2-(5-acetyl-4,7-dihydro-4,7-dioxobenzofuran-6-yl)oxymethyl-4-isopropyl-6-methoxysaccharin (0.13 g, 46.6% yield, m.r. 193°-195° C. with decomposition).

EXAMPLE 8

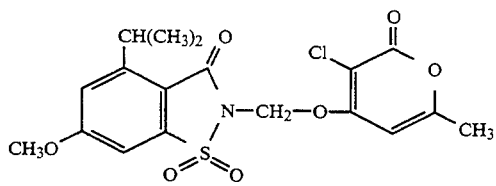

A mixture of 3-chloro-4-hydroxy-6-methyl-2H-pyran-2-one (0.493 g, 3.07 mmol), DMF and $K_2CO_3$ (0.467 g, 3.38 mmol) was stirred at room temperature under $N_2$ for 0.5 hours then 2-chloromethyl-4-isopropyl-6-methoxysaccharin (0.978 g, 3.22 mmol) was added in one portion. The mixture was stirred at room temperature for 3 hours, and then at 75° C. for 3 hours. The mixture was poured into water, extracted with ethyl acetate and the organic layer was washed with brine and dried. The solvent was removed in vacuo and the residue was purified by column chromatography on silica eluting with 30% ethyl acetate/hexane to afford 0.25 g (18.1%) of 2-(3-chloro-6-methyl-2-oxo-2H-pyran-4yl)oxymethyl-4-isopropyl-6-methoxysaccharin, m.p. 182.5°–183.5° C. after recrystallization from ether/hexane.

EXAMPLES 9A–9J

The compounds identified in Table III below were prepared by the following general procedure.

A mixture of the appropriate compound of Formula III (H—O—Z), about 1.0–1.5 equivalents of an appropriate base and an appropriate solvent was stirred at room temperature for about 0–60 minutes and then about 1.0–1.2 equivalents of an appropriate 2-chloromethyl-4-isopropyl-6-$R_2$-saccharin was added. The mixture was stirred at about room temperature to about 90° C. for about 1–48 hours and was worked up as follows: Method 1: the reaction mixture was poured into ice/water and was either (a) extracted with a suitable solvent (e.g. ethyl acetate, chloroform or methylene chloride) and the organic layer was separated, dried over $Na_2SO_4$, filtered and concentrated, and the residue thus obtained was purified as shown in Table III; or (b) the product precipitated from the ice/water and was collected by filtration and was purified as shown in Table III; or Method 2: the solvent was removed in vacuo and the residue was purified as shown in Table III.

TABLE III

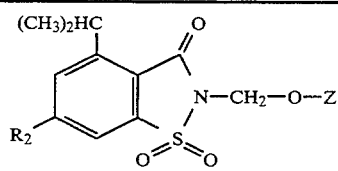

| Example | Z | $R_2$ | Base/Solvent | Work-Up Method | Melting Point (°C.)/Yield (%) | Recrystallization Solvent |
|---|---|---|---|---|---|---|
| 9A | ![structure] | $CH_3O$ | $K_2CO_3$ DMF | #1 | 211–213 9.3 | Water |
| 9B | ![structure] | $CH_3O$ | $K_2CO_3$ DMF | #1 | 197–200 | $Et_2O$/ $CH_3CN$[a] |
| 9C | ![structure] | $CH_3O$ | $K_2CO_3$ N-methyl-2-pyrrolidinone | #1 | 217–218 26 | EtOAc/ $Et_2O$/ |
| 9D | ![structure] | $CH_3O$ | $(iPr)_2NEt$ $CH_3CN$ | #1 | 250–252 31.8 | DMF/ Water[b] |

TABLE III-continued

| Example | Z | R₂ | Base/ Solvent | Work-Up Method | Melting Point (°C.)/ Yield (%) | Recrystallization Solvent |
|---|---|---|---|---|---|---|
| 9E | (pyrido-pyrimidinone with O(CH₂)₂N-pyrrolidine) | CH₃O | methyltriazabicyclodecene/CH₃CN | #1 | 228–230 (dec.) (HCl Salt) 43.5 | (C) |
| 9F | (pyridinone with N—CH₂C₆H₅) | CH₃O | methyltriazabicyclodecene | #2 | 176.5–178 22.8 | benzene/hexane[d] |
| 9G | (pyridopyrimidinone) | PhCH₂O (CH₂)₂O— | K₂CO₃ DMF | #1 | Foam 70 | (e) |
| 9H | (Cl-pyridopyrimidinone) | (iPr)₃SiO (CH₂)₂O | methyltriazabicyclodecene/DMF | #1 | Foam 31 | (f) |
| 9I | (Cl-pyridopyrimidinone) | H | (iPr)₂NEt DMF | #1 | 208.5–210 45.2 | EtOAc |
| 9J | (dimethyl-furanone with C₆H₅) | CH₃O | Methyltriazabicyclodecene/CH₃CN | #1 | 189–193 20.9 | Benzene/hexane[g] |

[a] Product was purified by column chromatography on silica eluting with 5% methanol/CHCl₃ prior to recrystallization.
[b] Product was purified by recrystallization from CH₃CN and then by column chromatography on silica eluting with 5% ethyl acetate/CH₂Cl₂ prior to this recrystallization.
(C) The free base of the product was purified by column chromatography on silica eluting with 65% ethyl acetate/30% methanol/5% triethylamine, prior to formation of the HCl salt by treatment with 4.6 N ethanolic HCl.
[d] Product was purified by column chromatography on silica eluting with hexane/ethyl acetate (3/1 to 2/1) prior to recrystallization.
(e) Product was purified by column chromatography on silica eluting with 60% ethyl acetate/hexane.
(f) Product was purified by column chromatography on silica eluting with 40% ethyl acetate/hexane.
[g] Product was purified by column chromatography on silica eluting with ethyl acetate/hexane (1/7) to (1/6) prior to recrystallization.

EXAMPLE 10

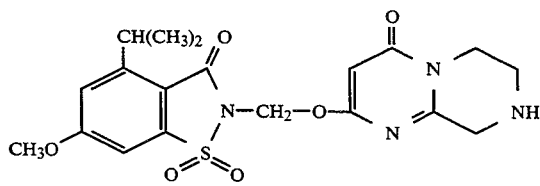

A mixture of the compound of Example 4H (0.359 g, 0.834 mmol), ethyl acetate (35 mL), and palladium on carbon was hydrogenated at 50 psi on a parr hydrogenator for 13/4 hours. Additional palladium on carbon (0.16 g) was added and the reaction was continued for an additional 2 hours. The catalyst was removed by filtration and the filtrate was concentrated in vacuo. The crude product was purified by column chromatography on silica eluting with EtOAc/MeOH/triethylamine (88.5/7.5/4) to afford 0.132 g (36.5%) of the desired product as the free base which was dissolved in ethanol, and treated with citric acid in ethanol to afford 0.142 g of the product as the citric acid salt, m.p. 198°-200° C.

EXAMPLE 11

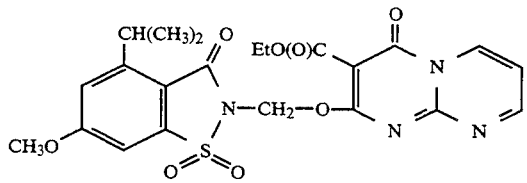

Ethyl 5-oxo-2-(pyrimidinyl-2-yl)-2,5-dihydro isoxaxole-4-carboxylate (0.70 g, 3.0 mmol) was added to a mixture of potassium t-butoxide (0.37 g, 3.3 mmol) in THF (20 mL) and the mixture was stirred at 40° C. under nitrogen for 0.5 hours. The solvent was removed in vacuo, and the residue was dried under high vacuum. The residue was mixed with DMF (20 mL) and treated with 2-chloromethyl-4-isopropyl-6-methoxysaccharin (0.91 g, 3.0 mmol) in DMF (5 mL). The mixture was stirred at room temperature for approximately 3 days, poured into ice/water and extracted with ethyl acetate. The organic layer was separated, dried over Na2SO4 and concentrated in vacuo. The residue was purified by column chromatography on silica eluting with 5% MeOH/EtOAc to afford 0.18 g (12%) of 2-[3-(ethoxycarbonyl)-4-oxo-4H-pyrimido[1,2-a] pyrimidin-2-yl]oxymethyl-4-isopropyl-6-methoxysaccharin, m.p. 189°-191° C. after recrystallization from toluene/hexane.

EXAMPLE 12

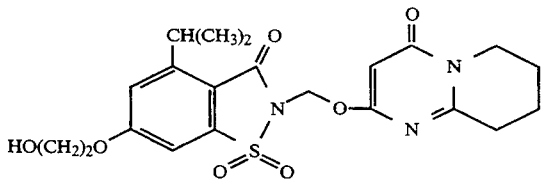

A mixture of the product of Example 9G (1.35 g) in ethyl acetate (200 mL)/methanol (5 mL) and 10% palladium on carbon (0.5 g) was hydrogenated at 50 psi on a parr hydrogenator for 3 hours. Additional palladium on carbon (0.5 g) was added and the mixture was hydrogenated for 8-9 hours. The mixture was filtered, the filtrate was concentrated in vacuo, and the residue was purified by column chromatography on silica eluting with ethyl acetate to afford 0.89 g of 2-[4-oxo-6,7,8,9-tetrahydro-4H-pyrido[1,2-a]pyrimidin-2-yl]oxymethyl-4-isopropyl-6-(2-hydroxyethoxy)saccharin as white foam.

EXAMPLE 13

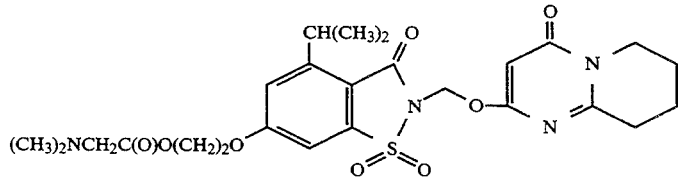

To a solution of the compound of Example 12 (0.8 g, 1.72 mmol) in CH2Cl2 (25 mL) containing 1,3-dicyclohexylcarbodiimide (1.06 g, 5.14 mmol) was added dimethyl glycine (0.19 g, 1.9 mmol), followed by 4-dimethylaminopyridine (0.21 g, 1.72 mmol). The mixture was stirred at room temperature for 2 hours, the solvent was removed in vacuo, and the residue was purified by column chromatography on silica eluting with 10% methanol/ethyl acetate to afford 0.64 g (68%) of 2-[4-oxo-6,7,8,9-tetrahydro-4H-pyrido-[1,2-a]pyrimidin-2-yl]oxymethyl-4-isopropyl-6-[2-(dimethylaminomethylcarbonyloxy)ethoxy]saccharin as a white foam.

EXAMPLE 14

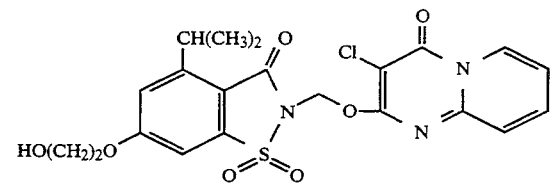

To suspension of the compound of Example 9H (0.76 g) in methanol (30 mL), was added THF, followed by 2N HCl (20-30 mL). The mixture was stirred for 4-5 hours, additional 2N HCl was added and the mixture was stirred overnight. The solvent was removed in vacuo, the residue was diluted with THF and treated with concentrated HCl (2 mL). After stirring for 5-6 hours, the solvent was removed in vacuo and the residue was extracted with ethyl acetate. The organic layer was washed with water, then brine and was dried. The solvent was removed in vacuo and the residue was purified by column chromatography on silica eluting with 80% ethyl acetate/hexane to afford 0.43 g of 2-[3-chloro-4-oxo-4H-pyrido[1,2-a]pyrimidin-2-yl]oxymethyl-4-isopropyl-6-[2-hydroxyethoxy]saccharin, m.p. 214.5°-215.5° C.

EXAMPLES 15A-15C

Following a procedure similar to that described in Example 9D, but substituting an appropriate compound of the Formula III (H—O—Z), it is contemplated that there can be prepared the following compounds of Formula I:

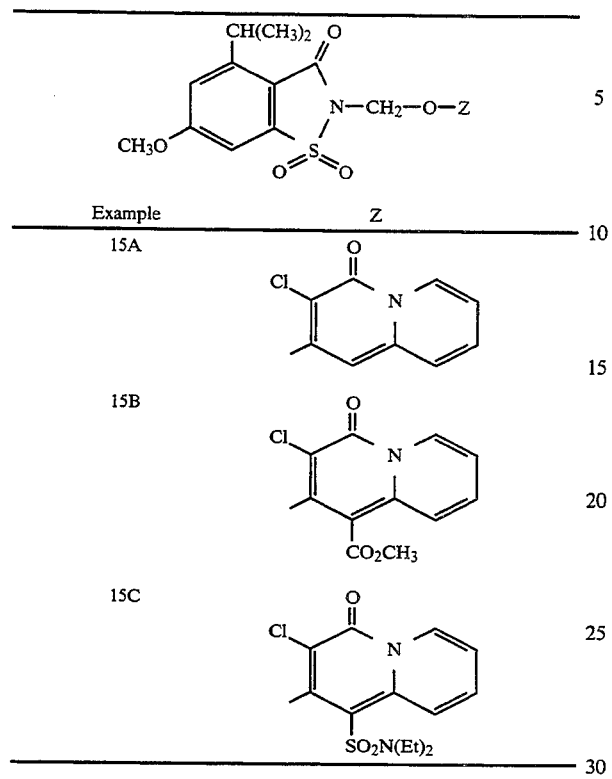

| Example | Z |
|---|---|
| 15A | |
| 15B | |
| 15C | |

EXAMPLE 16

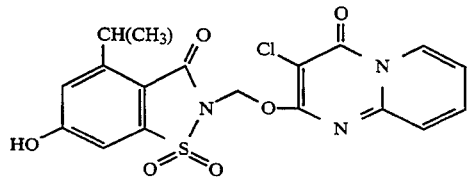

Following a procedure similar to that described in example 6 it is contemplated that there can be prepared 2-[3-chloro-4-oxo-4H-pyrido[1,2-a]pyrimidin-2-yl]oxymethyl-6-hydroxy-4-isopropylsaccharin from 3-chloropyrido[1,2-a]pyrimidine-2,4-dione (2 equivalents), methyltriazabicyclodecene (2 equivalents), DMF and 2-chloromethyl-4-isopropyl-6-hydroxysaccharin.

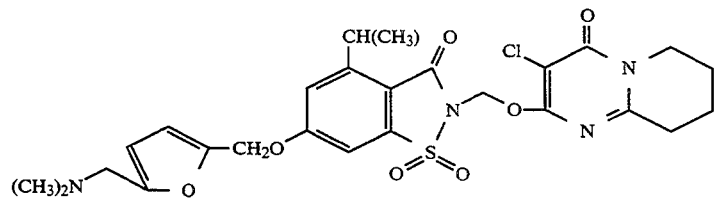

It is contemplated that 2-[3-chloro-4-oxo-4H-pyrido[1,2-a]pyrimidin-2-yl]oxymethyl-4-isopropyl-6-[1-(5-dimethylaminomethyl-2-furanyl)methoxy]saccharin can be prepared by treating a solution of 2-[3-chloro-4-oxo-4H-pyrido[1,2-a]pyrimidin-2-yl]-oxymethyl-6-hydroxy-4-isopropylsaccharin in DMF with triphenylphosphine, 5-dimethylaminomethyl-2-hydroxymethyl-furan and diethylazodicarboxylate.

EXAMPLE 17

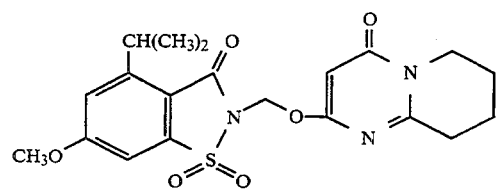

A mixture of the compound of Example 4C (0.3 g, 0.708 mmol), ethyl acetate (14 mL) and 10% palladium on carbon (0.3 g) was hydrogenated on a Parr hydrogenator at 50 psi for 7 hours. The reaction mixture was filtered through celite, the filtrate was concentrated in vacuo, and the residue was purified by column chromatography on silica eluting with 50% ethyl acetate/hexane to 70% ethyl acetate/hexane to afford 0.165 g (54%) of 2-[4-oxo-6,7,8,9-tetrahydro-4H-pyrido[1,2-a]pyrimidin-2-yl]oxymethyl-4-isopropyl-6-methoxysaccharin, m.p. 183.5°-185.5° C. after recrystallization from ethyl acetate/hexane.

EXAMPLE 18

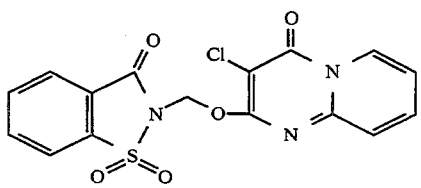

To a mixture of 2-hydroxy-3-chloropyrido[1,2-a]pyrimidine-4-one (0.324 g), and methyltriazabicyclodecene (0.24 mL) in DMF (15 mL) was added 2-bromomethylsaccharin (0.414 g). The mixture was stirred overnight, poured into water and the precipitate which formed was collected by filtration and recrystallized from DMF to afford 0.371 g (65%) of 2-[3-chloro-4-oxo-4H-pyrido[1,2-a]pyrido[1,2-a]pyrimidine-2-yl]oxymethyl-saccharin.

EXAMPLES 19(a) AND 19(b)

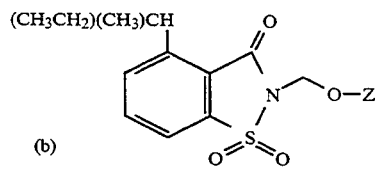

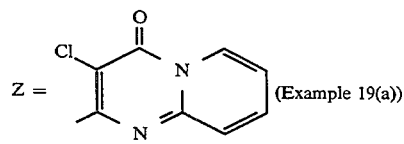

Z = 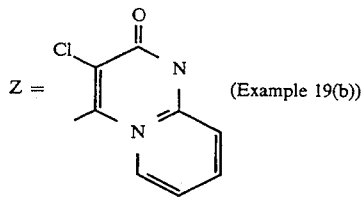 (Example 19(b))

To a mixture of 2-hydroxy-3-chloropyrido[1,2-a]pyrimidine-4-one-(6.29 g), and methyltriazabicyclodecene (0.22 mL) in DMF (12 mL) was added 2-chloromethyl-4-sec-butylsaccharin (0.39 g). The reaction mixture was stirred for 8 hours, poured into water and the precipitate which formed was collected by filtration. The solid residue was purified by column chromatography on silica eluting with hexane/ethyl acetate (2/1) to ethyl acetate/hexane (1/1) to afford 0.284 g (46.7%) of 2-[3-chloro-4-oxo-4H-pyrido[1,2-a]pyrimidine-2-yl]oxymethyl-4-sec-butylsaccharin, (Example 19a) m.p. 211°–212° C. after recrystallization from ethyl acetate; and 0.027 g of 2-[3-chloro-2-oxo-2H-pyrido[1,2-a]pyrimidine-4-yl]oxymethyl-4-sec-butylsaccharin, (Example 19b) m.p. 268°–271° C. (dec.) after recrystallization from $CH_2Cl_2$.

Further examples of compounds of Formula I can be prepared wherein —Z is any of the moieties described in Examples 1–7 or Example 8–15 and wherein $R_1$ is hydrogen, methyl, ethyl, n-propyl, 2-butyl, dimethylamino, methoxy, ethoxy, or isopropoxy and $R_2$ is hydrogen, 7-methyl, 6-(4-methyl-1-piperazinyl), 6-(1-methyl-2-pyrrolyl), 6-dimethylamino, 5-nitro, 6-nitro, 6-hydroxy, 7-hydroxy, 5-methoxy, 7-methoxy, 5,6-dimethoxy, 5,7-dimethoxy, 6,7-dimethoxy, 6-ethoxy, 6-isopropoxy, 6-cyclobutyloxy, 6-[2-(4-morpholinyl)ethoxy], 6-[(2,3-dihydroxy)propoxy], 6-[(2,3-propylenedioxy)-propoxy], 6-[2,3-dimethoxypropoxy], 6-[2-(2-methoxyethoxy)ethoxy], 7-[2-(2-methoxyethoxy)ethoxy], 7-carboxymethoxy, 6-methoxycarbonylmethoxy, 6-(t-butoxycarbonyl)methoxy, 6-benzyloxycarbonylmethoxy, 7-(t-butoxycarbonyl)-methoxy, 6-(2-hydroxyethoxy), 7-dimethylamino-carbonyloxy, 6,7-methylenedioxy, 6-fluoro, 7-chloro, 6-(n-propyl)-7-methoxy, 6-methyl-5,7-dimethoxy, 5-hydroxy-6-methoxy or 6-dimethylamino-7-chloro.

Biological Properties of the Compounds

As stated above the compounds of Formula I inhibit the enzymatic activity of proteolytic enzymes are useful in treatment of degenerative diseases. More particularly they inhibit human leukocyte elastase and chymotrypsin-like enzymes and are useful in treatment of emphysema, rheumatoid arthritis, pancreatitis, cystic fibrosis, chronic bronchitis, adult respiratory distress syndrome, inflammatory bowel disease, psoriasis, bullous pemphigoid and alpha-1-antitrypsin deficiency. This utility was demonstrated by an in vitro test of inhibition of compounds of Formula I against human leukocyte elastase.

Measurements of the inhibition constant ($K_i$) of a human leukocyte elastase inhibitor complex has been described (Cha, Biochemical Pharmacology, vol 24, pp. 2177–2185, 1975) for "truly reversible inhibition constants" usually concerning competitive inhibitors. The compounds of Formula I do not from truly reversible inhibitor complexes but rather are consumed by the enzyme to some extent. $K_i^*$, which is defined as the rate of reactivation of the enzyme divided by the rate of inactivation of the enzyme ($k_{off}/k_{on}$), was therefore determined instead. The values of $k_{off}$ and $k_{on}$ were measured and $K_i^*$ was then calculated.

The value of $k_{on}$ was determined by measuring the enzyme activity of an aliquot of the enzyme as a function of the time after addition of the test compound (inhibitor). By plotting the log of the enzyme activity against time an observed rate of inactivation ($k_{obs}$) was obtained by the equation $k_{obs}= \ln 2/t_{\frac{1}{2}}$ wherein $t_{\frac{1}{2}}$ is the time required for the enzyme activity to decrease by 50%. The value of $k_{on}$ was then obtained by the equation $k_{on}=k_{obs}/[I]$ wherein [I] is the concentration of the inhibitor. The value of $k_{off}$ was similarly determined, and $K_i^*$ was then obtained by the equation $K_i^*=k_{off}/k_{on}$.

The results shown in Table IV were obtained for compounds of Formula I of the examples.

TABLE IV

| Inhibition of Human Leukocyte Elastase | |
|---|---|
| Compound of Formula I of Example | $K_i^*$ (nM) |
| 1A | 0.4 |
| 1B | 0.22 |
| 1C | 0.7 |
| 1D | 0.25 |
| 1E | 0.035 |
| 1F | 0.22 |
| 1G | 0.05 |
| 1H | 0.027 |
| 1I | 0.25 |
| 1J | 0.85 |
| 1K | 0.013 |
| 1L | 0.09 |
| 1M | 0.18 |
| 1N | 0.052 |
| 1O | 0.016 |
| 1P | 0.041 |
| 1Q | 0.06 |
| 1R | 0.038 |
| 2 | 0.5 |
| 3A | 0.43 |
| 3B | 0.27 |
| 4A | 0.025 |
| 4B | 0.9 |
| 4C | 0.078 |
| 4D | 0.066 |
| 4E | 0.093 |
| 5 | 0.23 |
| 6 | 0.92 |
| 7 | 17 |

The human-leukocyte elastase inhibitory activity of representative compounds of the invention was also demonstrated by the following procedure:

The test compound (inhibitor) is dissolved in DMSO in a vial to produce an inhibitor stock solution which has a concentration in the range of 200–1000 μM. The inhibitor stock solution is diluted (1:4, 1:16 and 1:64) into assay vials (vials 1, 2 and 3 respectively) containing 2.4 mL of buffer solution (50 mM N-[2-hydroxyethyl]-piperazine-N'-[2-ethanesulfonic acid]/NaOH, 500 mM NaCl, pH 7.8 at 25° C.) and DMSO is added so that the total volume in each vial is 3.2 mL. 70 μL, 50 μL, 35 μL and 25 μL of inhibitor from assay vial 1 is placed into the first four wells of a 96-well microtiter plate and each well is made up to 90 μL total volume with the addition of a 25% DMSO/buffer solution. The inhibitor from assay vials 2 and 3 is processed in a similar manner and placed in wells 5–12 respectively to afford a total of 12 different inhibitor concentrations. Four wells (wells 13–16) containing 90 μL of the 25% DMSO/buffer solution but no inhibitor are also run simultaneously with the inhibited wells as a control. 150 μL of substrate solution (prepared by the addition of 500 μL of the human leukocyte elastase (HLE) substrate MeOSuc-Ala-Ala-Pro-Val-pNA (18.7 mM in DMSO) to 19.5 mL of buffer solution) was then added simultaneously into each of the 16 wells and the solution in each well was thoroughly mixed.

The 96-well microtiter plate was placed into a Microplate Reader #89815A spectrophotometer 110 μL of the enzyme solution (prepared as follows: a mixture of 20 mL of buffer solution and 20 mg of bovine serum albumen is gently vortexed in a scintillation vial and 5 μL HLE stock solution (1 mg/mL dissolved in deionized water) is added simultaneously to each of the 16 wells. Each of the solutions in the wells is thoroughly mixed and then the time-dependent absorbance data is collected at an absorbance of 410 mM until the assay is complete. It should be noted that although this assay method can be done manually, it is preferred to perform the assay robotically using a Hewlett Packard MicroAssay System Robot.

A plot of the absorbance versus time data thus obtained affords progress curves the final slope of which is equal to the final steady-state velocities ($V_F$). Using the program ENZFITTER (Elsevier software), the progress curves for the four control assays ([I]=0) are fit by linear regression to yield the enzyme velocity values in the absences of inhibitor ($V_o$) which are averaged to produce a single fixed value. The inhibition constant $K_i$(nM) is then obtained from a plot of $$\frac{[I]}{1 - V_F/V_o} \text{ versus } V_o/V_F$$

which affords a linear plot wherein:

$$\text{slope} = K_i\left(1 + \frac{[S]}{K_m}\right)$$

and [S] is the concentration of the substrate and $K_m$ is the Michaelis constant.

The following Table summarizes the results obtained from the testing of representative compounds of the invention utilizing this latter method.

TABLE V

| Inhibition of Human Leukocyte Elastase | |
|---|---|
| Compound of Formula I of Example | $K_i$ (nM) |
| 1S | 0.22 |
| 1T | 0.083 |
| 1U | 0.078 |
| 1V | 0.033 |
| 1W | 0.034 |
| 4F | 0.08 |
| 4G | 0.20 |
| 4H | 0.066 |
| 4I | 0.19 |
| 4J | 0.120 |
| 4K | 2.5 |
| 8 | 0.025 |
| 9A | 0.044 |
| 9B | 0.12 |
| 9C | 0.058 |
| 9D | 0.081 |
| 9E | 0.035 |
| 9F | 0.138 |
| 9G | 0.140 |
| 9I | 0.210 |
| 9J | 0.021 |
| 10 | 0.120 |

TABLE V-continued

| Inhibition of Human Leukocyte Elastase | |
|---|---|
| Compound of Formula I of Example | $K_i$ (nM) |
| 11 | 0.40 |
| 12 | 0.130 |
| 13 | 0.063 |
| 14 | 0.095 |
| 17 | 0.110 |
| 18 | 14.0 |
| 19a | 0.72 |
| 19b | 4.7 |

Method of Use and Compositions

The proteolytic enzyme inhibiting amount of the compound of Formula I can be estimated from the results of the test for human leukocyte elastase inhibition and can additionally be varied for a particular patient depending on the physical condition of the patient, the route of administration, the duration of treatment and the response of the patient. An effective dose of the compound of Formula I can thus only be determined by the clinician after consideration of all pertinent criteria and exercise of best judgment on behalf of the patient.

A compound of Formula I can be prepared for pharmaceutical use by incorporating it in a pharmaceutical composition for oral, parenteral or aerosol inhalation administration, which can be in solid or liquid dosage form including tablets, capsules, solutions, suspensions and emulsions and which can include one or more suitable adjuvants. Solid unit dosages in the form of tablets or capsules for oral administration are preferred. For this purpose the adjuvant can be for example one or more of calcium carbonate, starch, lactose, talc, magnesium stearate and gum acacia. The compositions are prepared by conventional pharmaceutical techniques.

We claim:

1. A compound having the structural formula:

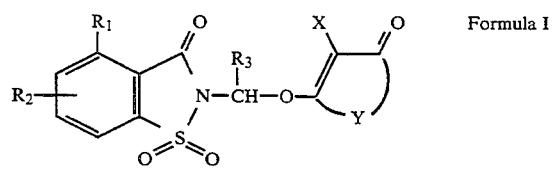

Formula I wherein
R₁ is hydrogen, halo, lower-alkyl, perfluoro-lower-alkyl, perchloro-lower-alkyl, lower-alkenyl, lower-alkynyl, cyano, amino, lower-alkylamino, di-lower-alkylamino, lower-alkoxy, benzyloxy, lower-alkoxycarbonyl or phenyl; and R₂ is from one to three substituents at any or all of the 5-, 6- and 7-positions and is selected from the group consisting of hydrogen, lower-alkyl, cycloalkyl, amino-lower-alkyl, lower-alkylamino-lower-alkyl, di-lower-alkylamino-lower-alkyl, hydroxy-lower-alkyl, lower-alkoxy-lower-alkyl, perfluoro-lower-alkyl, perchloro-lower-alkyl, formyl, cyano, carboxy, aminocarbonyl, R-oxycarbonyl, B=N, 1-lower-alkyl-2-pyrrolyl, lower-alkylsulfonylamino, perfluoro-lower-alkylsulfonylamino, perchloro-lower-alkylsulfonylamino, nitro, hydroxy, R-carbonyloxy, lower-alkoxy, cycloalkoxy, B=N-lower-alkoxy, hydroxy-lower-alkoxy, poly-hydroxy-lower-alkoxy or acetal or ketal thereof, lower-alkoxy-lower-alkoxy, poly-lower-alkoxy-loweralkoxy, hydroxy-poly-lower-alkylenoxy, lower-alkoxy-poly-lower-alkylenoxy, B=N-carbonyloxy, carboxy-lower-alkoxy, R-oxycarbonyl-lower-alkoxy, methylenedioxy, di-lower-alkyl-phosphonyloxy, R-thio, R-sulfinyl, R-sulfonyl, perfluoro-lower-alkylsulfonyl, perchloro-lower-alkylsulfonyl, aminosulfonyl, lower-alkylaminosulfonyl, di-lower-alkylaminosulfonyl, halo, B=N—(CH$_2$)$_p$C(O)O(CH$_2$)$_{p'}$—O—, —O—(CH$_2$-)$_p$—(5—((CH$_2$)$_{p'}$—B=N—2-furanyl), and R-oxy-lower-alkoxy wherein p and p' are integers from 1 to 4, R is lower-alkyl, phenyl or phenyl-lower-alkyl, phenyl can have from one to three substituents selected from the group consisting of lower-alkyl, B=N-carbonyl, B=N, lower-alkoxy, B=N-lower-alkoxy and halo and B=N is amino, lower-alkylamino, di-lower-alkylamino, carboxy-lower-alkylamino, 1-pyrrolidinyl, 1-piperidinyl, 1-azetidinyl, 4-morpholinyl, 1-piperazinyl, 4-lower-alkyl-1-piperazinyl, 4-benzyl-1-piperazinyl or 1-imidazolyl;

R$_3$ is hydrogen, lower-alkyl or phenyl;

X is hydrogen, nitro, halo, lower-alkyl, perfluoro-lower-alkyl, perchloro-lower-alkyl, phenyl, phenyl-lower-alkyl, phenylcarbonyl, pyridyl-lower-alkyl, formyl, lower-alkanoyl, carboxy, lower-alkoxycarbonyl, aminocarbonyl, lower-alkylaminocarbonyl, di-lower-alkylaminocarbonyl, cyano, B=N, B=N-lower-alkyl, B=N-lower-alkanoyl, B=N-lower-alkoxycarbonyl, hydroxy, lower-alkoxy, phenyloxy, B=N-lower-alkoxy, lower-alkylthio, phenylthio, lower-alkylsulfonyl, phenylsulfonyl or B=N-sulfonyl wherein phenyl is unsubstituted or has from one to three substituents selected from the group consisting of lower-alkyl, lower-alkoxy and halo and B=N is amino, lower-alkylamino, di-lower-alkylamino, carboxy-lower-alkylamino, 1-pyrrolidinyl, 1-piperidinyl, 1-azetidinyl, 4-morpholinyl, 1-piperazinyl, 4-lower-alkyl-1-piperazinyl, 4-benzyl-1-piperazinyl or 1-imidazolyl; and —Y— is the remaining atoms of a monocyclic or bicyclic, substituted or unsubstituted carbocyclic or oxygen or sulfur containing heterocyclic ring system;

or a pharmaceutically acceptable acid addition salt thereof if the compound has a basic functional group or a pharmaceutically acceptable base addition salt thereof if the compound has an acidic functional group.

2. A compound according to claim 1 wherein:

R$_1$ is hydrogen, halo, lower-alkyl, perfluoro-lower-alkyl, perchloro-lower-alkyl, lower-alkenyl, lower-alkynyl, cyano, amino, lower-alkylamino, di-lower-alkylamino, lower-alkoxy, benzyloxy, lower-alkoxycarbonyl or phenyl; and R$_2$ is from one to three substituents at any or all of the 5-, 6- and 7-positions and is selected from the group consisting of hydrogen, lower-alkyl, cycloalkyl, amino-lower-alkyl, lower-alkylamino-lower-alkyl, di-lower-alkylamino-lower-alkyl, hydroxy-lower-alkyl, lower-alkoxy-lower-alkyl, perfluoro-lower-alkyl, perchloro-lower-alkyl, formyl, cyano, carboxy, aminocarbonyl, R-oxycarbonyl, B=N, 1-lower-alkyl-2-pyrrolyl, lower-alkylsulfonylamino, perfluoro-lower-alkylsulfonylamino, perchloro-lower-alkylsulfonylamino, nitro, hydroxy, R-carbonyloxy, lower-alkoxy, cycloalkoxy, B=N-lower-alkoxy, hydroxy-lower-alkoxy, poly-hydroxy-lower-alkoxy or acetal or ketal thereof, lower-alkoxy-lower-alkoxy, poly-lower-alkoxy-lower-alkoxy, hydroxy-poly-lower-alkylenoxy, lower-alkoxy-poly-lower-alkylenoxy, B=N-carbonyloxy, carboxy-lower-alkoxy, R-oxycarbonyl-lower-alkoxy, methylenedioxy, di-lower-alkyl-phosphonyloxy, R-thio, R-sulfinyl, R-sulfonyl, perfluoro-lower-alkylsulfonyl, perchloro-lower-alkylsulfonyl, aminosulfonyl, lower-alkylaminosulfonyl, di-lower-alkylaminosulfonyl and halo wherein R is lower-alkyl, phenyl or phenyl-lower-alkyl, phenyl can have from one to three substituents selected from the group consisting of lower-alkyl, B=N-carbonyl, B=N, lower-alkoxy, B=N-lower-alkoxy and halo and B=N is amino, lower-alkylamino, di-lower-alkylamino, carboxy-lower-alkylamino, 1-pyrrolidinyl, 1-piperidinyl, 1-azetidinyl, 4-morpholinyl, 1-piperazinyl, 4-lower-alkyl-1-piperazinyl, 4-benzyl-1-piperazinyl or 1-imidazolyl;

R$_3$ is hydrogen, lower-alkyl or phenyl;

X is hydrogen, nitro, halo, lower-alkyl, perfluoro-lower-alkyl, perchloro-lower-alkyl, phenyl, phenyl-lower-alkyl, phenylcarbonyl, pyridyl-lower-alkyl, formyl, lower-alkanoyl, carboxy, lower-alkoxycarbonyl, aminocarbonyl, lower-alkylaminocarbonyl, di-lower-alkylaminocarbonyl, cyano, B=N, B=N-lower-alkyl, B=N-lower-alkanoyl, B=N-lower-alkoxycarbonyl, hydroxy, lower-alkoxy, phenyloxy, B=N-lower-alkoxy, lower-alkylthio, phenylthio, lower-alkylsulfonyl, phenylsulfonyl or B=N-sulfonyl wherein phenyl is unsubstituted or has from one to three substituents selected from the group consisting of lower-alkyl, lower-alkoxy and halo and B=N is amino, lower-alkylamino, di-lower-alkylamino, carboxy-lower-alkylamino, 1pyrrolidinyl, 1-piperidinyl, 1-azetidinyl, 4-morpholinyl, 1-piperazinyl, 4-lower-alkyl-1-piperazinyl, 4-benzyl-1-piperazinyl or 1-imidazolyl; and —Y— is the remaining atoms of a monocyclic or bicyclic, substituted carbocyclic or oxygen or sulfur containing heterocyclic ring system;

or a pharmaceutically acceptable acid addition salt thereof if the compound has a basic functional group or a pharmaceutically acceptable base addition salt thereof if the compound has an acidic functional group.

3. A compound according to claim 2 wherein —Y— is —(CH$_2$)$_m$—, —C(=O)—, —(CH$_2$)$_m$—O—, —CHR—O—, —CR$_2$—O—, —C[(CH$_2$)$_n$]—O—, —C(R')=C(R')—O—, —C(=O)—C(R'')=C(R'')—, —C(Z')=C(Z')—, or —C(Z')=C(Z')—O—, wherein m is 1, 2, 3, or 4, n is 3, 4, or 5, R is the same or different lower-alkyl, phenyl or phenyl-lower-alkyl, R' is the H or R, R'' is H or R or the R'' groups taken together with the carbon atoms to which they are bonded are furano, the Z' groups taken together with the carbon atoms to which they are bonded are benzo, or furano, wherein phenyl, benzo, or furano, can have from one to three substituents selected from the group consisting of lower-alkyl, B=N-carbonyl, B=N, lower-alkoxy, B=N-lower-alkoxy and halo wherein B=N is amino, lower-alkylamino, di-lower-alkylamino, (carboxy-lower-alkyl-)amino, 1-pyrrolidinyl, 1-piperidinyl, 1-azetidinyl, 4-morpholinyl, 1-piperazinyl, 4-lower-alkyl-1-piperazinyl, 4-benzyl-1-piperazinyl or 1-imidazolyl.

4. A compound according to claim 3 wherein R$_1$ is lower-alkyl, R$_2$ is hydrogen, R-oxycarbonyl-lower-alkoxy or lower-alkoxy, R$_3$ is hydrogen and X is hydrogen, halo, lower-alkyl, phenyl, phenyl-lower-alkyl, phenylcarbonyl, lower-alkanoyl, B=N, B=N-lower-alkyl, phenyloxy, or lower-alkoxycarbonyl.

5. A compound according to claim 4 wherein $R_1$ is lower-alkyl, $R_2$ is hydrogen or lower-alkoxy, $R_3$ is hydrogen and X is hydrogen, halo, lower-alkyl, phenyl, phenyl-lower-alkyl, phenylcarbonyl, lower-alkanoyl, B=N, B=N-lower-alkyl or phenyloxy.

6. A compound according to claim 5 wherein $R_1$ is isopropyl, $R_2$ is hydrogen or 6-methoxy and X is hydrogen, chloro, methyl, phenyl, phenylmethyl, phenylcarbonyl, acetyl, 1-piperidinyl, 4-morpholinylmethyl or phenoxy.

7. A compound according to claim 6 having the structural formula

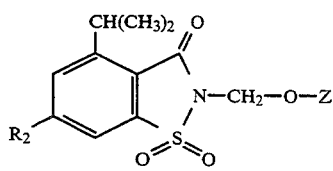

wherein $R_2$ is hydrogen or methoxy and —Z has one of the following structural formulas:

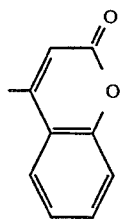 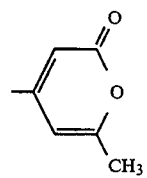 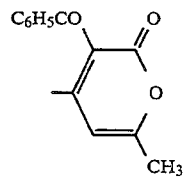

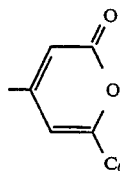 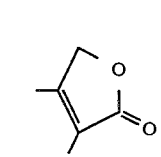 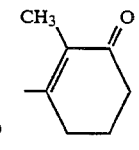

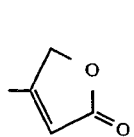 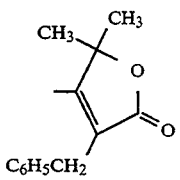 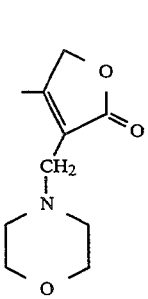

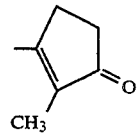 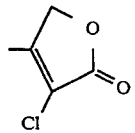 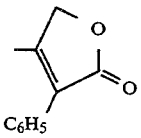

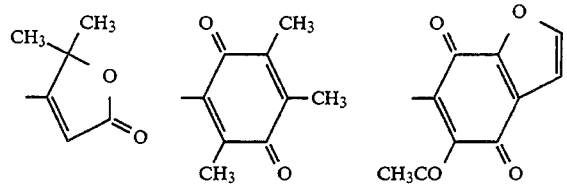

8. A compound according to claim 7 wherein $R_1$, is isopropyl or sec-butyl; $R_2$ is hydrogen, 6-benzyloxycarbonylmethoxy, or 6-methoxy; and X is hydrogen, chloro, bromo, ethoxycarbonyl, 4-morpholinylmethyl, phenyl or phenylmethyl.

9. A compound according to claim 8 wherein the structural formula:

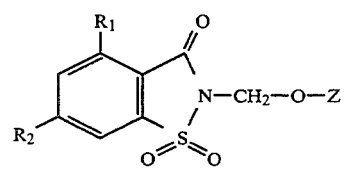

wherein $R_1$ is isopropyl or sec-butyl; $R_2$ is hydrogen, benzyloxycarbonylmethoxy, or methoxy and —Z has one of the following structural formulas:

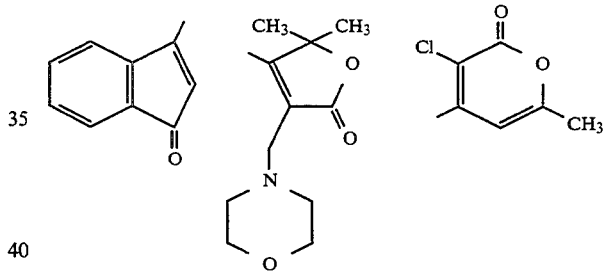

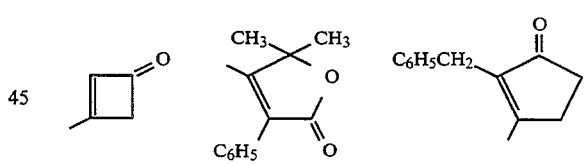

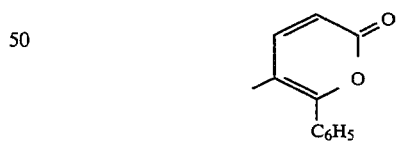

10. A compound according to claim 2 wherein —Y— is C(Z''')=C(Z''')—S,—and wherein the Z'''groups taken together with the carbon atoms to which they are bonded are benzo.

11. A compound according to claim 10 wherein $R_1$ is lower-alkyl; $R_2$ is lower-alkoxy or hydroxy-lower-alkoxy; $R_3$ is hydrogen; and X is hydrogen, halo, lower-alkyl, phenyl, phenyl-lower-alkyl, phenylcarbonyl, lower-alkanoyl, B=N, B=N-lower-alkyl, phenyloxy, or lower-alkoxycarbonyl.

12. A compound according to claim 11 wherein $R_1$ is isopropyl; $R_2$ is 6-methoxy or 6-hydroxyethoxy; and X is hydrogen, or chloro.

13. A compound according to claim 12 wherein the structural formula:

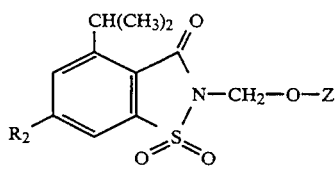

wherein R$_2$ methoxy or hydroxyethoxy and Z is:

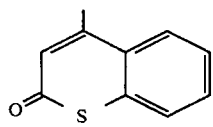

14. A compound according to claim 1 wherein R$_2$ is selected from the group consisting of B═N—(CH$_2$)$_p$-C(O)O(CH$_2$)$_p'$—O— and R-oxy-lower-alkoxy.

15. A compound according to claim 14, wherein —Y— is —(CH$_2$)$_m$—, —C(═O)—, —(CH$_2$)$_m$—O—, —CHR—O—, —CR$_2$—O—, —C[(CH$_2$)$_n$]—O—, —C(R')═C(R')—O—, —C(═)—C(R")═C(R")—, —C(Z')═C(Z')—, —C(Z')═C(Z')—O—, or C(Z''')—C(Z''')—S—, and wherein the Z''' groups taken together with the carbon atoms to which they are bonded are benzo; m is 1, 2, 3, or 4, n is 3, 4, or 5, R is the same or different lower-alkyl, phenyl or phenyl-lower-alkyl, R' is H or R, R" is H or R or the R" groups taken together with the carbon atoms to which they are bonded are furano, the Z' groups taken together with the carbon atoms to which they are bonded are benzo, or furano, wherein phenyl, benzo, or furano can have from one to three substituents selected from the group consisting of lower-alkyl, B═N-carbonyl, B═N, lower-alkoxy, B═N-lower-alkoxy and halo wherein B═N is amino, lower-alkylamino, di-lower-alkylamino, (carboxy-lower-alkyl)amino, 1-pyrrolidinyl, 1-piperidinyl, 1-azetidinyl, 4-morpholinyl, 1-piperazinyl, 4-lower-alkyl-1-piperazinyl, 4-benzyl-1-piperazinyl or 1-imidazolyl.

16. A compound according to claim 15 wherein R$_1$, is lower-alkyl; R$_2$ is di-lower-alkylamino-(CH$_2$)$_p$C(O)O(CH$_2$)$_p'$—O or phenyl-lower-alkyloxy-lower-alkoxy; R$_3$ is hydrogen; and X is hydrogen, halo, lower-alkyl, phenyl, phenyl-lower-alkyl, phenylcarbonyl, B═N, B═N-lower-alkyl, phenyloxy, or lower-alkoxycarbonyl.

17. A compound according to claim 16 wherein R$_1$ is isopropyl; R$_2$ is 6-dimethylamino-CH$_2$C(O)O(CH$_2$)$_2$—O— or 6-benzyloxyethoxy; and X is hydrogen.

18. A pharmaceutical composition for treatment of degenerative disease which comprises a proteolytic enzyme inhibiting concentration of a compound of Formula I according to claim 1 in a pharmaceutical carrier.

19. A pharmaceutical composition for treatment of degenerative disease which comprises a proteolytic enzyme inhibiting concentration of a compound of Formula I according to claim 2 in a pharmaceutical carrier.

20. A pharmaceutical composition for treatment of degenerative disease which comprises a proteolytic enzyme inhibiting concentration of a compound of Formula I according to claim 3 in a pharmaceutical carrier.

21. A pharmaceutical composition for treatment of degenerative disease which comprises a proteolytic enzyme inhibiting concentration of a compound of Formula I according to claim 5 in a pharmaceutical carrier.

22. A pharmaceutical composition for treatment of degenerative disease which comprises a proteolytic enzyme inhibiting concentration of a compound of Formula I according to claim 6 in a pharmaceutical carrier.

23. A pharmaceutical composition for treatment of degenerative disease which comprise a proteolytic enzyme inhibiting concentration of a compound of Formula I according to claim 7 in a pharmaceutical carrier.

24. A pharmaceutical composition for treatment of degenerative disease which comprise a proteolytic enzyme inhibiting concentration of a compound of Formula I according to claim 9 in a pharmaceutical carrier.

25. A pharmaceutical composition for treatment of degenerative disease which comprise a proteolytic enzyme inhibiting concentration of a compound of Formula I according to claim 10 in a pharmaceutical carrier.

26. A pharmaceutical composition for treatment of degenerative disease which comprise a proteolytic enzyme inhibiting concentration of a compound of Formula I according to claim 14 in a pharmaceutical carrier.

27. The method of treating a patient having a degenerative disease which comprises administering to the patient a proteolytic enzyme inhibiting amount of a compound of Formula I according to claim 1.

28. The method of treating a patient having a degenerative disease which comprises administering to the patient a proteolytic enzyme inhibiting amount of a compound of Formula I according to claim 2.

29. The method of treating a patient having a degenerative disease which comprises administering to the patient a proteolytic enzyme inhibiting amount of a compound of Formula I according to claim 3.

30. The method of treating a patient having a degenerative disease which comprises administering to the patient a proteolytic enzyme inhibiting amount of a compound of Formula I according to claim 5.

31. The method of treating a patient having a degenerative disease which comprises administering to the patient a proteolytic enzyme inhibiting amount of a compound of Formula I according to claim 6.

32. The method of treating a patient having a degenerative disease which comprises administering to the patient a proteolytic enzyme inhibiting amount of a compound of Formula I according to claim 7.

33. The method of treating a patient having a degenerative disease which comprises administering to the patient a proteolytic enzyme inhibiting amount of a compound of Formula I according to claim 9.

34. The method of treating a patient having a degenerative disease which comprises administering to the patient a proteolytic enzyme inhibiting amount of a compound of Formula I according to claim 10.

35. The method of treating a patient having a degenerative disease which comprises administering to the patient a proteolytic enzyme inhibiting amount of a compound of Formula I according to claim 14.

36. The method of treating a patient having a degenerative disease which comprises administering to the patient a proteolytic enzyme inhibiting amount of a composition according to claim 18.

37. The method of treating a patient having a degenerative disease which comprises administering to the patient a proteolytic enzyme inhibiting amount of a composition according to claim 19.

38. The method of treating a patient having a degenerative disease which comprises administering to the patient a proteolytic enzyme inhibiting amount of a composition according to claim 20.

39. The method of treating a patient having a degenerative disease which comprises administering to the patient a proteolytic enzyme inhibiting amount of a composition according to claim 21.

40. The method of treating a patient having a degenerative disease which comprises administering to the patient a proteolytic enzyme inhibiting amount of a composition according to claim 22.

41. The method of treating a patient having a degenerative disease which comprises administering to the patient a proteolytic enzyme inhibiting amount of a composition according to claim 23.

42. The method of treating a patient having a degenerative disease which comprises administering to the patient a proteolytic enzyme inhibiting amount of a composition according to claim 24.

43. The method of treating a patient having a degenerative disease which comprises administering to the patient a proteolytic enzyme inhibiting amount of a composition according to claim 25.

44. The method of treating a patient having a degenerative disease which comprises administering to the patient a proteolytic enzyme inhibiting amount of a composition according to claim 26.

* * * * *